(12) United States Patent
Sardesai et al.

(10) Patent No.: US 10,518,055 B2
(45) Date of Patent: *Dec. 31, 2019

(54) APPARATUS AND METHOD TO PROVIDE BREATHING SUPPORT

(71) Applicants: Rajendra Gurudas Sardesai, Arcadia, CA (US); Rangasamy Ramanathan, La Canada Flintridge, CA (US)

(72) Inventors: Rajendra Gurudas Sardesai, Arcadia, CA (US); Rangasamy Ramanathan, La Canada Flintridge, CA (US)

(73) Assignee: Eupnea Technologies Inc., South Pasadena, CA (US)

( * ) Notice: Subject to any disclaimer, the term of this patent is extended or adjusted under 35 U.S.C. 154(b) by 906 days.

This patent is subject to a terminal disclaimer.

(21) Appl. No.: 15/095,404

(22) Filed: Apr. 11, 2016

(65) Prior Publication Data

US 2016/0220779 A1 Aug. 4, 2016

Related U.S. Application Data

(63) Continuation of application No. 14/468,320, filed on Aug. 25, 2014, now Pat. No. 9,345,850.

(51) Int. Cl.
*A61M 16/20* (2006.01)
*A61M 16/06* (2006.01)
(Continued)

(52) U.S. Cl.
CPC .... *A61M 16/0666* (2013.01); *A61M 16/0875* (2013.01); *A61M 16/201* (2014.02);
(Continued)

(58) Field of Classification Search
CPC ............ A61M 16/003; A61M 16/0006; A61M 16/208; A61M 16/0875; A61M 16/20;
(Continued)

(56) References Cited

U.S. PATENT DOCUMENTS 3,710,780 A 1/1973 Milch
3,811,671 A 5/1974 Turnbull
(Continued)

FOREIGN PATENT DOCUMENTS

CH 687296 A5 * 11/1996 ............. A63B 23/18
EP 0 234 736 A1 9/1987
(Continued)

OTHER PUBLICATIONS

Singhal, Nalini et al., "Newborn Resuscitation in Resource-Limited Settings" Seminars in Fetal & Neonatal Medicine, 2008, pp. 432-439, vol. 13.
(Continued)

*Primary Examiner* — Samchuan C Yao
*Assistant Examiner* — Margaret M Luarca
(74) *Attorney, Agent, or Firm* — Rajendra Sardesai

(57) ABSTRACT

A ventilator, or a breathing assistance apparatus, is disclosed to ventilate patients who may have breathing difficulties, said device comprising a inspiratory pressure control duct configured to be immersed in a first body of fluid; a positive end-expiratory pressure control duct configured to be immersed in a second body of fluid; at least one valve connected to the peak inspiratory pressure control duct and to the positive end-expiratory pressure control duct, and at least one controller communicably connected to the valve to control rate of cycling of the valve, thereby controlling number of breaths per minute, and to control the duration of peak inspiratory pressure also known as inspiratory time.

21 Claims, 12 Drawing Sheets

(51) Int. Cl.
*A61M 16/08* (2006.01)
*A61M 16/10* (2006.01)
*A61M 16/00* (2006.01)

(52) U.S. Cl.
CPC ........ *A61M 16/202* (2014.02); *A61M 16/204* (2014.02); *A61M 16/205* (2014.02); *A61M 16/0096* (2013.01); *A61M 16/1045* (2013.01); *A61M 2016/0039* (2013.01); *A61M 2205/3334* (2013.01); *A61M 2205/3348* (2013.01)

(58) Field of Classification Search
CPC ............. A61M 16/00; A63B 21/00065; A63B 21/0084; A63B 23/18
See application file for complete search history.

(56) References Cited

U.S. PATENT DOCUMENTS

| | | |
|---|---|---|
| 3,977,395 A | 8/1976 | Brawn |
| 4,011,866 A | 3/1977 | Klein et al. |
| 4,459,983 A | 7/1984 | Beyreuther et al. |
| 4,471,773 A | 9/1984 | Bunnell et al. |
| 4,481,944 A | 11/1984 | Bunnell |
| 4,679,551 A | 7/1987 | Anthony |
| 4,805,612 A | 2/1989 | Jensen |
| 4,838,259 A | 6/1989 | Gluck et al. |
| 4,941,469 A | 7/1990 | Adahan |
| 5,156,776 A | 10/1992 | Loedding et al. |
| 5,271,388 A | 12/1993 | Whitwam et al. |
| 5,307,795 A | 5/1994 | Whitwam et al. |
| 5,632,268 A | 5/1997 | Ellis et al. |
| 5,752,506 A | 5/1998 | Richardson |
| 6,086,822 A | 7/2000 | Trinidad |
| 6,105,572 A | 8/2000 | Shaffer et al. |
| 6,591,835 B1 | 7/2003 | Blanch |
| 6,669,057 B2 * | 12/2003 | Saidman .............. B05C 5/001 222/146.5 |
| 6,805,120 B1 | 10/2004 | Jeffrey et al. |
| 7,077,154 B2 | 7/2006 | Jacobs et al. |
| 7,191,780 B2 | 3/2007 | Faram |
| 8,381,723 B2 | 2/2013 | DiBlasi et al. |
| 8,499,759 B2 | 8/2013 | DiBlasi et al. |
| 2004/0069304 A1 | 4/2004 | Jam |
| 2005/0072470 A1 | 4/2005 | Jacobs et al. |
| 2006/0078506 A1 | 4/2006 | Niven et al. |
| 2007/0221116 A1 | 9/2007 | Kruse |
| 2009/0056719 A1 | 3/2009 | Newman, Jr. |
| 2011/0073112 A1 | 3/2011 | DiBlasi et al. |
| 2011/0079222 A1 | 4/2011 | DiBlasi et al. |
| 2012/0220817 A1 * | 8/2012 | Castillon Levano .. A61G 10/02 600/22 |

FOREIGN PATENT DOCUMENTS

| | | | |
|---|---|---|---|
| EP | 0 513 712 A1 | 11/1992 | |
| WO | WO-9706843 A1 * | 2/1997 | ............ A61M 16/00 |
| WO | WO 2005/035019 A2 | 4/2005 | |

OTHER PUBLICATIONS

Morley, C.J. et al., "Nasal Continous Positive Airway Pressure: Does Bubbling Improve Gas Exchange?" Arch Dis Child Fetal Neonatal Ed, 2005, pp. F343-F344, vol. 90.
Pillow, J. Jane et al., "Bubble Continuous Positive Airway Pressure Enhances Lung Volume and Gas Exchange in Preterm Lambs", Am J Resp Crit Care Med, 2007. pp. 63-69, vol. 176.
Reyburn, Brent et al., "Nasal Ventilation Alters Mesenchymal Cell Turnover and Improves Aleolarization in Preterm Lambs" Am J Resp & Crit Care Med, 2008, pp. 407-418, vol. 178.
Narasimhan, R. et al, "A Review of Non-Invasive Ventilation Support in Neonates" Paediatrics & Child Health, 2013, pp. 7-11, vol. 24, No. 1.
Lawn, Joy E. et al,"4 Million Neonatal Deaths. When? Where? Why?" Lancet, Mar. 2005, pp. 891-900. vol. 365.
Koyamaibole, Lanieta et al, "An evaluation of Bubble-CPAP in Neonatal Unit in a Developing Country" Journal of Tropical Pediatrics, 2006, pp. 249-253, vol. 52, No. 4.
Nekvasil, R. et al., "High Frequency "Bubble" Oscillation Ventilation in the Neonatal Period" Cesk. Pediatr., 1992, pp. 465-470, vol. 47, No. 8 Abstract.
International Search Authority, Form 206,PCT/US 14/53736 dated Dec. 18, 2014, See p. 2, Form 206(extra Sheet), Consideration regarding Unity of Invention and Obviousness.
International Search Authority, International Search Report and Written Opinion,PCT/US 14/53736 dated Feb. 18, 2015.
Ramanathan, R. et al, "Non-Invasive Ventilation and Surfactant Therapy" J Pulmon Resp Med, 2013, pp. 1-7, vol. S13.
Chan, KM et al., "The Use of Bubble CPAP in Premature Infants: Local Experience", Hong Kong Journal of Paediatrics, Dec. 31, 2007, pp. 86-92, vol. 12, No. 2.
Ammari, Amer et al, "Bubble nasal CPAP manual" Riyadh AL-Kharj Hospital Programme Neonatal Intensive Care 2005, XP-002541077, Dec. 31, 2005.
Lee, Kyong-Soon et al., "A Comparison of Underwater Bubble CPAP with Ventilator-Derived CPAP in Premature Neonates Ready for Extubation" Biol Neonate, 1998, pp. 69-75, vol. 73.
Narendran, Vivek et al., "Early Bubble CPAP and Outcomes in ELBW Preterm Infants", Journal of Perinatology, 2003, pp. 195-199, vol. 23.
Garg, S. et al, "Non-Invasive Ventilation in Premature Infants: Based on Evidence or Habit" J. Clin. Neonatology, 2013, pp. 155-159, vol. 2, No. 4.
Diblasi, R, "Nasal Continuous Posistive Airway Pressure (CPAP) for Respiratory Care of Newborn Infant", Selezion Arir de Respiratory Care e AARC Times, 2010, pp. 3-29, No. 1.
Pillow, J. Jane et al., "Bubble CPAP: Is the Noise Important? An In Vitro Study" Pediatric Research, 2005, pp. 826-830, vol. 57, No. 6.
Diblasi, Robert et al, "Noninvasive Respiratory Support of Juvenile Rabbits by High-Amplitude Bubble CPAP" Pediatr Res 2010, pp. 624-629, vol. 67, No. 6.
Diblasi, Robert et al, "Effective Gas Exchange in Paralyzed Juvenile Rabbits Using Simple, Inexpensive Respiratory Support Devices" Pediatr Res 2010, pp. 526-530, vol. 68, No. 6.

* cited by examiner

APPARATUS AND METHOD TO PROVIDE BREATHING SUPPORT

CROSS-REFERENCE TO RELATED APPLICATIONS

This application is a continuation of co-pending U.S. patent application Ser. No. 14/468,320, filed Aug. 25, 2014; which claims the benefit of the earlier filing dates of U.S. Provisional Patent Application No. 61/874,323, filed Sep. 5, 2013; U.S. Provisional Patent Application No. 61/929,947, filed Jan. 21, 2014; and these patent applications are incorporated herein by reference.

FIELD

Embodiments described herein concern devices and methods that assist gas exchange and stabilize lung volume in patients of all ages with breathing problems.

BACKGROUND

Patients who have breathing difficulties are conventionally provided breathing assistance using mechanical ventilators. These devices are generally expensive and out of reach of a large portion of the population, particularly in economically disadvantaged countries. These devices also require substantial training and expertise to operate and maintain. Further, these devices do not provide the user the ability to set and vary upper limit of safe positive pressure that is patient specific and commensurate with the peak inspiratory pressure levels set during ventilation in an easy and less expensive way using a fluid column.

In recent years, there has been increasing interest in the development of breathing assistance devices that are less expensive. U.S. Pat. No. 8,499,759 discloses the use of a two-way valve in a pressure regulating breathing assistance apparatus wherein the valve is placed intermediate two pressure control conduits that are submerged at varying lengths in a single container containing a fluid. In such apparatus, depending on the size of the valve, back pressure is generated whereby the pressure of gas at a patient interface may be higher than the pressure set using one of the control conduits, but not the other. This back pressure, if not correctly accounted for, has important treatment and safety implications if the device is used on a patient. Further, when two pressure control conduits are located in the same container, the interaction between the two conduits in operation may impact pressures at a patient interface.

There is a significant need to provide a respiratory assistance apparatus that is easy and less expensive to make, operate and maintain, and has high-positive-pressure safety feature that is simple, reliable and easily adjustable relative to the desired patient-specific inspiratory pressure level.

SUMMARY OF THE INVENTION

It is generally known in the medical profession that stabilization of lung volumes and improvement in gas exchange in patients receiving ventilation assistance could be achieved through appropriate settings and control of the positive pressures generated, amplitude and frequency of oscillating positive pressure in the ventilator. Embodiments described herein provide the user a device and method to set pressures, oscillations, amplitude and frequency, and further allows the user to set the upper limit of positive pressure that is specific for a patient to reduce the likelihood of damage to the lungs. Additionally, the embodiments described herein maintain a patient's mean airway pressure at controlled levels. Device parameters such as levels of fluid in the containers, lengths of the ducts immersed in the fluids in the containers can be varied to control the high as well as low pressures. These embodiments also have features that allow a user to select and modulate breaths per minute, inspiratory time, and the ratio of inspiratory to expiratory time. The embodiments described herein are useful to adults, children and newborn babies. Further, the embodiments can be used during transport of patients, and may be used in facilities that do not have access to mechanical ventilators. Several embodiments described herein can also be converted to a bubble Continuous Positive Airway Pressure (CPAP) system.

In one embodiment, a ventilator system is provided having a pressurized gas supply, two containers filled with fluid, and a primary duct with two ends—the proximal end and the distal end. The proximal end is connected to the pressurized gas supply. The primary duct is adapted for connection to a patient interface between the proximal and distal ends. At the distal end, a peak inspiratory pressure control duct is connected and immersed in a body of fluid in the first container. A positive end-expiratory pressure control duct is also connected to the distal end of the duct and immersed in the body of fluid in the second container. A two-port valve, also known as a two-way valve, is connected in between the inspiratory pressure control duct and the positive end-expiratory pressure control duct wherein the rate of opening and closing of the valve can be controlled. In addition, at least one safety duct is connected to the primary duct near the proximal end and is immersed in the fluid column in the first container at depth greater than the immersed length of the peak inspiratory pressure control duct. Immersed length is the vertical distance measured from the top of the fluid surface to the tip of a pressure control duct. The depth to which the at least one safety duct is immersed is controlled by the user. In some embodiments, ducts have simple markings, for example in cm of water, to help the user set high pressure (peak inspiratory pressure), low pressure (positive end-expiratory pressure), and high-pressure limit (Pop-Off). In other embodiments, the immersed length is adjusted by varying water column heights or by varying positions of ducts or both to deliver high and low pressures. In certain embodiments, as a safety feature, the default position of the ventilator system is to deliver the lower pressure at all times as CPAP when the ventilator system is connected to the patient.

The use of double containers allows the user to isolate and fix any issues with one container or duct without disconnecting the patient from the breathing support. Also, the use of double containers prevents the bubbles generated in one container from impacting the liquid column level and pressure in the duct placed in the other container. In some embodiments, two-way or three-way valve allows the user to set breathing rates from 4-60 per minute, known as conventional mechanical breaths, and frequencies in the range of 60-900 per minute, known as high frequency range. In other embodiments, a controller allows the user to control inspiratory to expiratory ratios or have it fixed as percent of cycle time to maintain a desired inspiration time to expiration time ratio, when the cycle frequencies are adjusted. Valves used in the embodiments include without limitation solenoid valves, pneumatic valves and solar powered valves.

In another embodiment, a ventilator system is provided having a pressurized gas supply, two containers filled with fluid, and a primary duct with two ends—the proximal end and the distal end. The proximal end is connected to the pressurized gas supply. The primary duct is adapted for connection to a patient interface between the proximal and distal ends. Also provided is a three-port valve (also known as a three-way valve) having one inlet port and two outlet ports. The distal end of the primary duct is connected to the inlet port of the valve. The first outlet port of the valve is connected to a peak inspiratory pressure control duct that is immersed in a body of fluid in the first container. The second outlet port of the valve is connected to a positive end-expiratory pressure control duct that is immersed in a body of fluid in the second container. In operation, the valve alternatively connects the inlet port to the first outlet port and the second outlet port, i.e., the gas entering the inlet port passes through the first outlet port for a period of time and then the gas entering the inlet port passes through the second outlet port for another period of time, completing a cycle of passage of gas through the first outlet port and the second outlet port. The cycle then repeats. A controller communicably connected to the valve controls the number of cycles per unit time, for example, number of cycles per minute. In addition, at least one safety duct is connected to the primary duct near the proximal end and is immersed in the body of fluid in the first container at depth greater than the immersed length of the peak inspiratory pressure control duct.

In yet another embodiment, a second valve is also provided wherein the second valve is an open-shut type shutoff valve which can isolate the positive end-expiratory pressure control duct from the remainder of the ventilator gas flow circuit.

In some embodiments, the two containers are of the same size and the tips of the peak inspiratory pressure control and the positive end-expiratory pressure control ducts are positioned at same location within each of the two containers. The location is determined by vertical distance of the tip of a control duct from the bottom inner surface of a container. In this embodiment, the peak inspiratory pressure and the positive end-expiratory pressure are set by a user by changing the fluid levels in the two containers.

In another embodiment, the level of fluid in the first container is greater than the level of fluid in the second container such that the immersed length of the peak inspiratory pressure control duct is greater than the immersed length of the positive end-expiratory pressure control duct.

In certain embodiments, the fluid used is water. In other embodiments, the peak inspiratory pressure control duct and the end-expiratory pressure control duct are substantially circular having an inside diameter of between about 0.5 to 2 cm and their immersed lengths inside the containers are in the range of about 2-50 cm.

DETAILED DESCRIPTION

Figure 1:
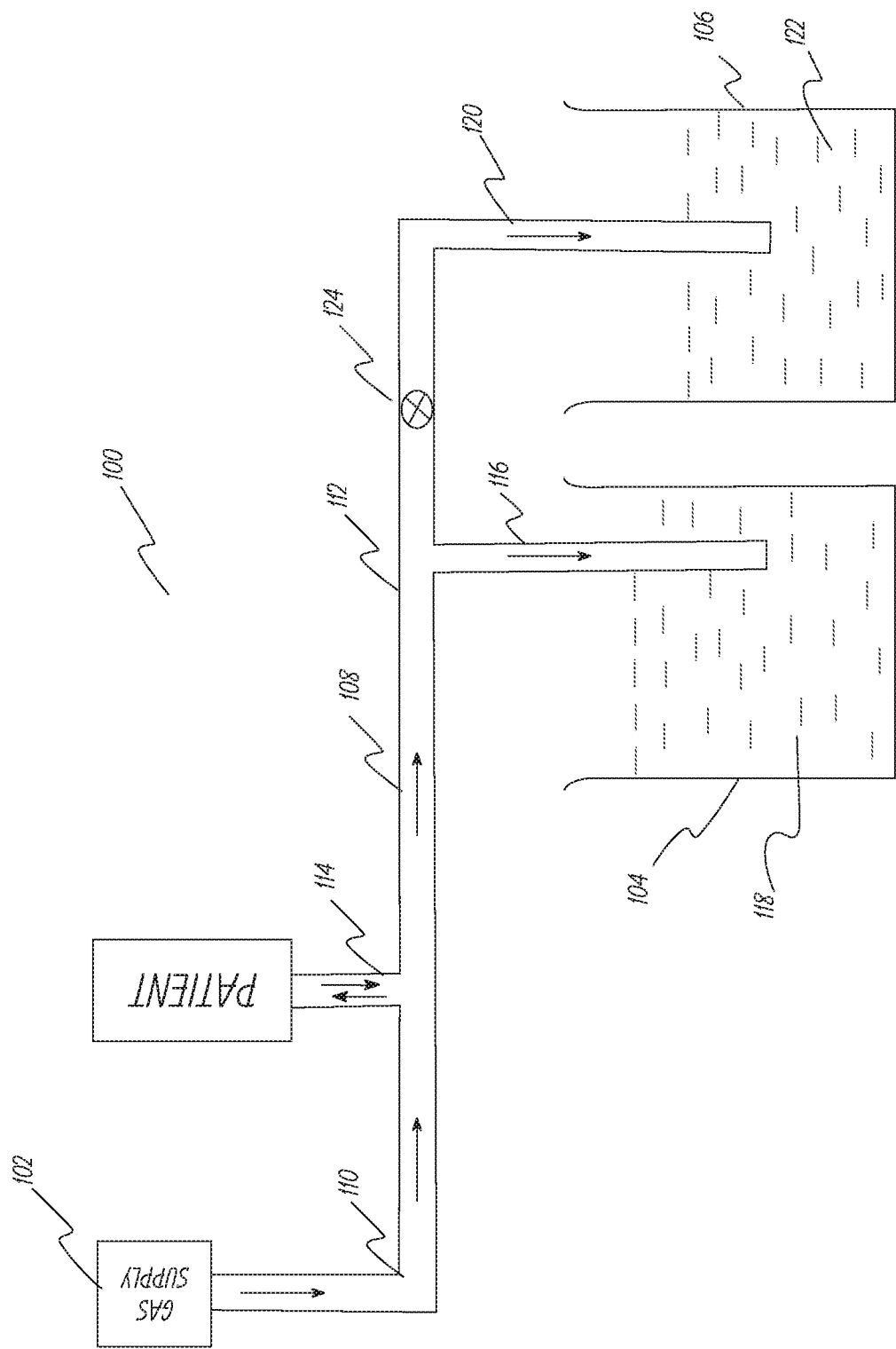
FIG. 1 depicts a ventilator system utilizing a peak inspiratory pressure control duct immersed in fluid in a first container; a positive end-expiratory pressure control duct immersed in fluid in a second container; one two-port valve located in-between the peak inspiratory pressure control duct and the positive end-expiratory pressure control duct; and the height of the column of fluid in the first container is greater than the height of the column of fluid in the second container. Based on the durations of valve open and shut times, low as well high frequency breathing support can be delivered at fixed or variable ratio of inspiratory to expiratory time.

Embodiments described herein provide the user a device and method to set high and low pressures, oscillations, amplitude and frequency and further allows the user to set the upper limit of positive pressure that is specific for a patient to reduce the likelihood of damage to the lungs. Device parameters such as levels of fluid in the containers, lengths of the ducts immersed in the fluid in the containers can be varied to control the pressures. These embodiments also have features that allow the user to select and modulate breaths per minute, inspiratory time, and the ratio of inspiratory to expiratory time. The embodiments described herein are useful for patients of all ages including adults, children and newborn babies. Further, the embodiments can be used during transport of patients of all ages and in facilities that do not have access to mechanical ventilators. In operation, pressurized gas is released from the gas supply into the primary duct of the ventilator system disclosed in FIGS. 1-12, and the gas is delivered to a patient FIG. 1 illustrates a patient ventilation system 100 having a pressurized gas supply 102, two containers 104 and 106 filled with fluid, and a primary duct 108 with two ends—the proximal end 110 and the distal end 112. The proximal end 110 is connected to the pressurized gas supply 102. The duct 108 is adapted for connection to a patient interface 114 between the proximal end 110 and distal end 112. At the distal end 112, at least one peak inspiratory pressure (PIP) control duct 116 is connected and immersed in a body of fluid 118 in the first container 104. At least one positive end-expiratory pressure (PEEP) control duct 120 is also connected to the distal end 112 of the duct and immersed in the body of fluid 122 in the second container 106. A two-port valve 124 is connected in between the inspiratory pressure control duct and the positive end-expiratory pressure control duct. The valve 124 cycles from open to shut position and back to open position, and the rate of cycling of the valve can be controlled by a controller (not shown) communicably connected to the valve. The failure mode of the valve 124 is the open position whereby the gas flow is directed to the positive end expiratory pressure (PEEP) control duct 120 and the pressure at the patient interface 114 is maintained at the lower or baseline level.

In one embodiment, the two containers 104 and 106 are of the same height measured from the bottom inner surface of the container to the top opening of the container, and the distal ends (tips) of the peak inspiratory pressure control duct 116 and the positive end-expiratory pressure control duct 120 are at same vertical distance from the from the bottom inner surfaces of the two containers 104 and 106 respectively. The level of fluid in the first container 104 is greater than the level of fluid in the second container 106 whereby immersed length which is the vertical distance measured from the top of the fluid surface to the tip of a pressure control duct is greater for the peak inspiratory pressure control duct 116 than for the positive end-expiratory pressure control duct 120. In other embodiment, the height of the container 104 is greater than the height of container 106. In yet another embodiment, the level of fluid in container 104 is about the same as the level of fluid in container 106.

In certain embodiments, the two containers are identical in shape and size, and the ducts are pre-positioned in the containers at identical locations. The advantage of having identical containers with identically positioned PIP and PEEP control ducts is the ease of fabrication and operation. In other embodiments, the two containers are similar in shape and size and the ducts are pre-positioned in the containers at similar locations. In certain embodiments, the peak inspiratory pressure control duct and the end-expiratory pressure control duct are substantially circular having an inside diameter of between about 0.5-3 cm and the immersed length inside the containers is in the range of about 2-50 cm. The immersed vertical length of PIP and PEEP control ducts can be measured as the vertical distance from the fluid surface to the distal ends of the ducts. In all embodiments, the immersed vertical length of the PIP and PEEP control ducts can be adjusted to any value by adding or removing fluid to adjust fluid level, by sliding the ducts up and down to adjust the duct location, or doing both.

In some embodiments of the PIP and PEEP control ducts, the diameters of the ducts are about 0.5 cm to 2 cm. In other embodiments, more than one PIP control duct and more than one PEEP control duct may be used. In yet other embodiments, the PIP and PEEP control ducts may each have substantially similar lengths and diameters or different lengths and diameters. The lengths and cross-sectional shapes of the primary duct, the PIP control duct, and the PEEP control duct are preferably short and substantially circular or slightly oval in shape. However, any or all of the ducts can have any length or cross-sectional shape including but not limited to square, rectangular, triangular etc., without departing from the spirit of the present disclosure.

The fluid may comprise any number of suitable fluids or liquids exhibiting a wide range of densities, masses and viscosities including but not limited to water, or water with added vinegar to reduce the likelihood of bacterial contamination of the water.

A gas supply provides pressurized medical grade gas to the ventilator system including to the primary duct, patient duct, PIP control duct and PEEP control duct. Gas delivered by the gas supply may comprise atmospheric gases or any combination, mixture, or blend of suitable gases, including but not limited to atmospheric air, oxygen, nitrogen, helium, or combinations thereof. The gas supply may comprise a gas compressor, a container of pressurized gases, a substantially portable container of pre-pressurized gases, a gas-line hookup (such as found in a hospital) or any other suitable supply of pressurized gas, or combinations thereof. The gas supply is preferably controlled or configured to have a variable gas flow rates that can be controlled by user and adjusted according to the individual requirements of each patient. The patient ventilation system or gas supply may also include one or more flow control devices (not shown) including but not limited to a mechanical valve, an electronically controlled mechanical valve, a rotameter, a pressure regulator, a flow transducer, or combinations thereof. Gas flow rates, which are commonly used in the art, typically range from about 2 liters/minute (L/min) to about 15 L/min. However, these embodiments allow any flow rates of gas set by the user. For example, larger patients may require larger gas flows. Increasing the flow rates could result in the delivery of higher pressures; however, by setting the high-pressure blow-out level of the safety duct to a safe level, one can avoid inadvertent delivery of excessively high pressures to the patient.

A Heat and Moisture Exchanger (not shown) can also be included in the patient ventilation system to control the temperature and humidity of gas delivered to the patient interface. Continuous flow of gas in the delivery duct also prevents the patient from re-breathing gases exhaled from the lungs.

Referring to FIG. 1, the patient interface 114 can be invasive or non-invasive, including but not limited to face or nasal masks, nasal prongs, nasal cannula, short tube(s) placed in the nasal or naso-pharynx, endotracheal tubes, tracheostomy tubes, or combinations thereof. The two-port valve 124 may comprise a mechanical or electromechanical valve. The two-port valve 124 may be electronically controlled or mechanically controlled such that the user is able to set the ventilation rate and inspiratory time or the ratio of inspiratory to expiratory time. The two-port valve 124 is preferably "normally open" such that in the event of failure the valve would remain open and the patient would be subjected to the lower or baseline pressure. When the two-port valve 124 is open, gases flow through PEEP control duct 120, which is set in the container 106 with lower level of fluid than the container 104 having the PIP control duct 116, thereby controlling the positive end expiratory pressure in the circuit. When the two-port valve 124 is closed, gas in the pressurized circuit flows through PIP control duct 116, which is set in a container 104 with higher level of fluid than the container 106 having the PEEP control duct 120, thereby raising the pressure to peak inspiratory pressure and delivering a "mandatory breath" to the patient. The valve 124 can then be opened again to allow the patient to exhale, and the process may be repeated. In this manner, a patient can receive peak inspiratory pressure and positive end expiratory pressure (Bi-PAP ventilation) or intermittent positive pressure ventilation (IPPV). In some embodiments, any number of valves, PIP control ducts and PEEP control ducts can be used to provide different levels of high and low pressures.

Figure 2:
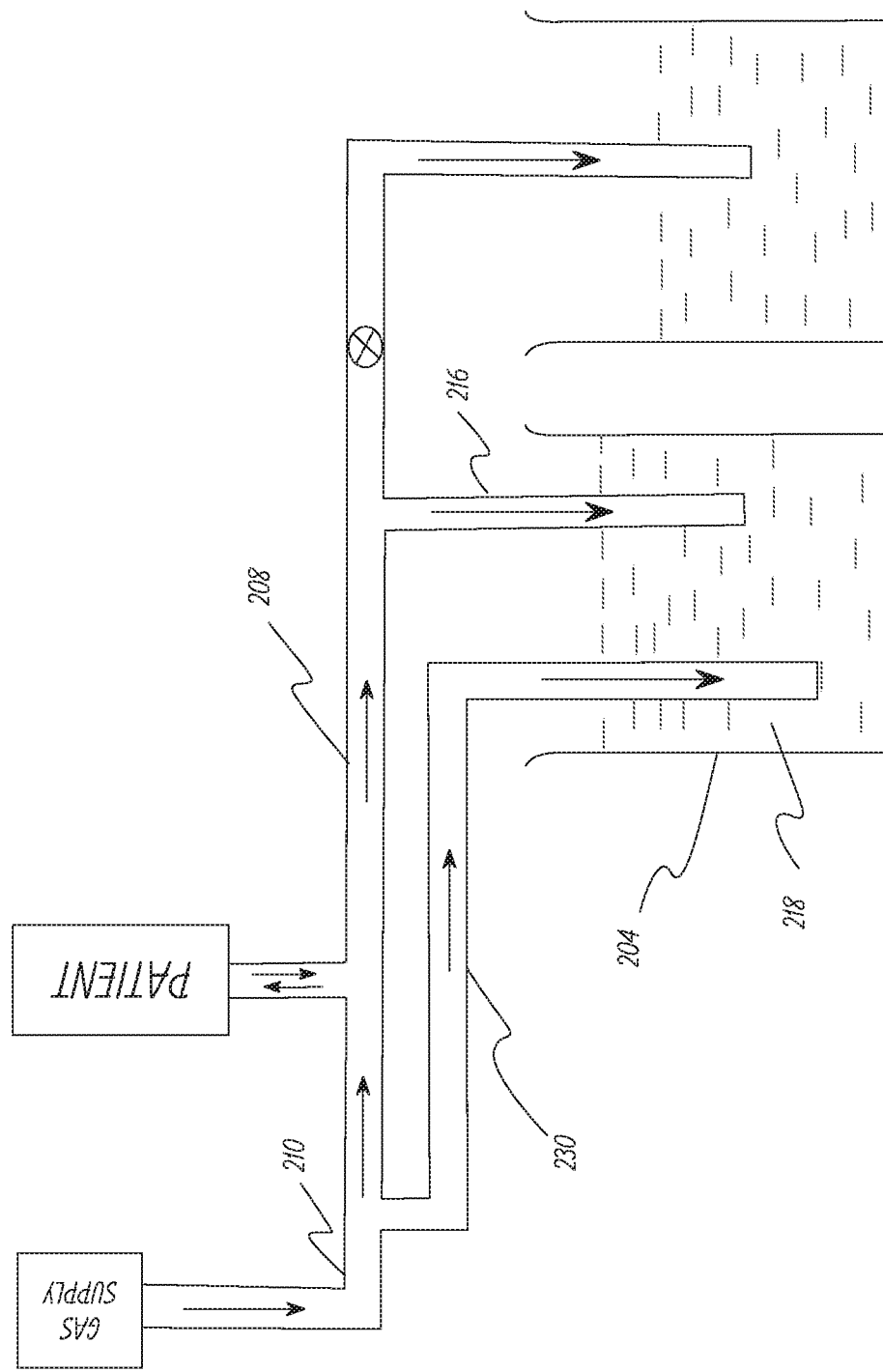
FIG. 2 depicts a ventilator system utilizing a peak inspiratory pressure control duct immersed in fluid in a first container; a positive end-expiratory pressure control duct immersed in fluid in a second container; one two-port valve located in-between the peak inspiratory pressure control duct and the positive end-expiratory pressure control duct; one high pressure safety duct immersed in fluid in the first container at a depth greater than the immersed length of the peak inspiratory pressure control duct; and the height of the column of fluid in the first container is greater than the height of the column of fluid in the second container.

FIG. 2 illustrates a ventilator system similar to FIG. 1, but has in addition, at least one safety duct 230. The safety duct 230 is connected to the primary duct 208 near the proximal end 210 of the primary duct 208. The safety duct 230 is immersed in the body of fluid 218 in the first container 204 at depth greater than the immersed length of the peak inspiratory pressure control duct 216. The safety duct allows setting the limit of a safe pressure relative to the set PIP pressure. For example, in some embodiments the fluid used is water, and the difference in vertical distance between the tip of the immersed safety duct 230 and the immersed PIP control duct 216 can be set at 5 cm if the user wants the maximum pressure that the lungs may be subjected to be not greater than the set PIP pressure by 5 cm of water.

Figure 3:
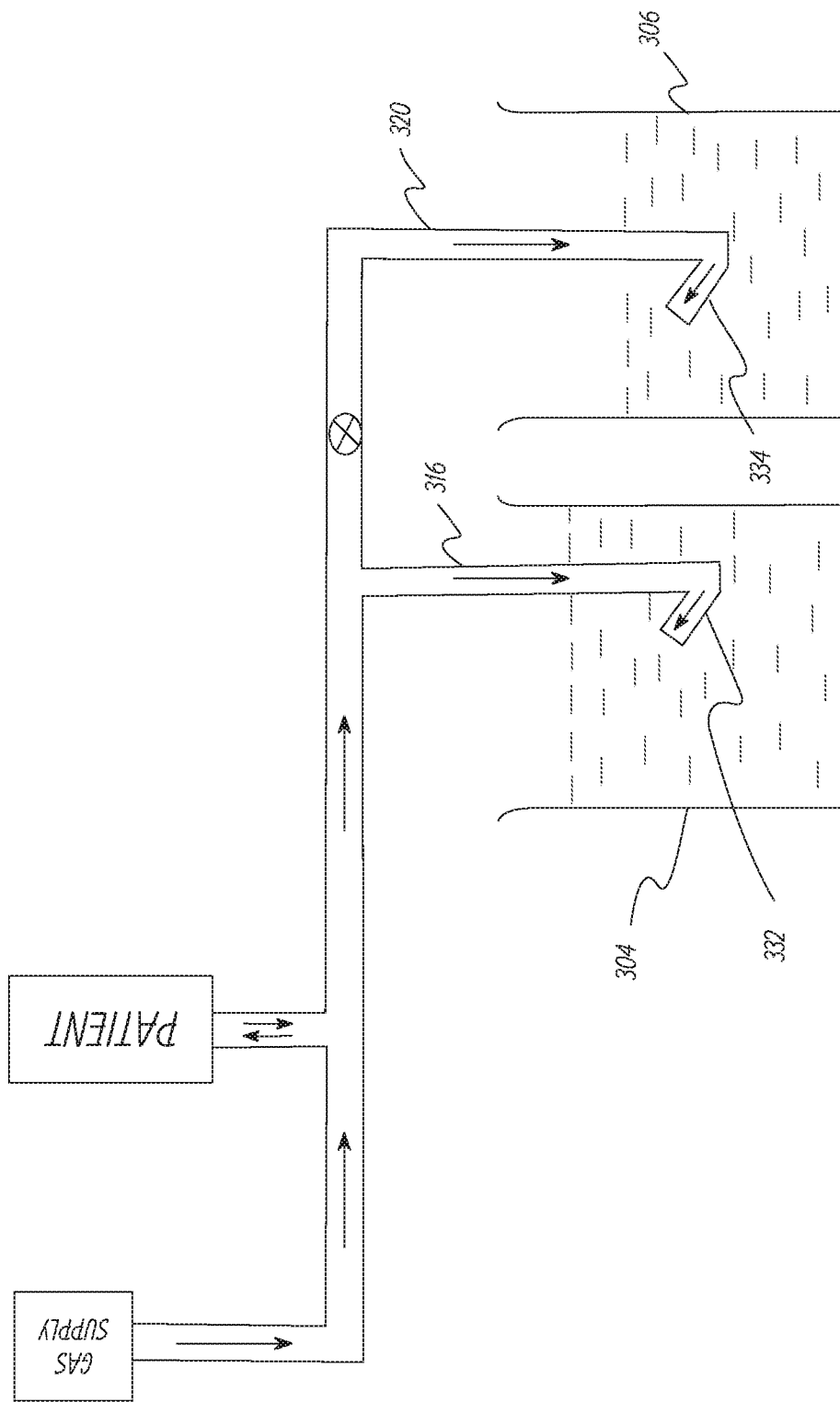
FIG. 3 depicts a ventilator system as shown in FIG. 1 with angled portions added to the peak inspiratory pressure control duct and the positive end-expiratory pressure control duct.

FIG. 3 illustrates a patient ventilator system similar to that illustrated in FIG. 1 utilizing a PIP control duct 316 in the first container 304 and a PEEP control duct 320 in the second container 306. The ducts 316 and 320 are immersed in fluid and configured to modulate airway pressures in a patient receiving Bi-PAP or IPPV. The embodiment illustrated in FIG. 3 further comprises two angled sections 332 and 334 connected to the distal ends of the PIP and PEEP control ducts respectively. The angle of angled section may be altered between 0 and 180 degrees to the vertical to control the amplitude and frequency of airway pressure oscillations that are superimposed on top of the airway pressure wave form for both the inhalation and exhalation cycles. In some embodiments, the angled arm of the angled section has length of between 2 cm and 10 cm. In other embodiments, more than two angled sections may be used. In one embodiment, the angles of the two or more angled sections may be substantially similar. In other embodiments, the angles of the two or more angled sections may be different. In one embodiment, the diameter of the angled section is the same as the diameter of the PIP and PEEP control ducts. In another embodiment, the diameter of the angled section is different from the diameter of the PIP and PEEP control ducts. The immersed vertical length of PIP and PEEP control ducts can be measured as the vertical distance from the fluid surface to the elbow of the angled section.

Figure 4:
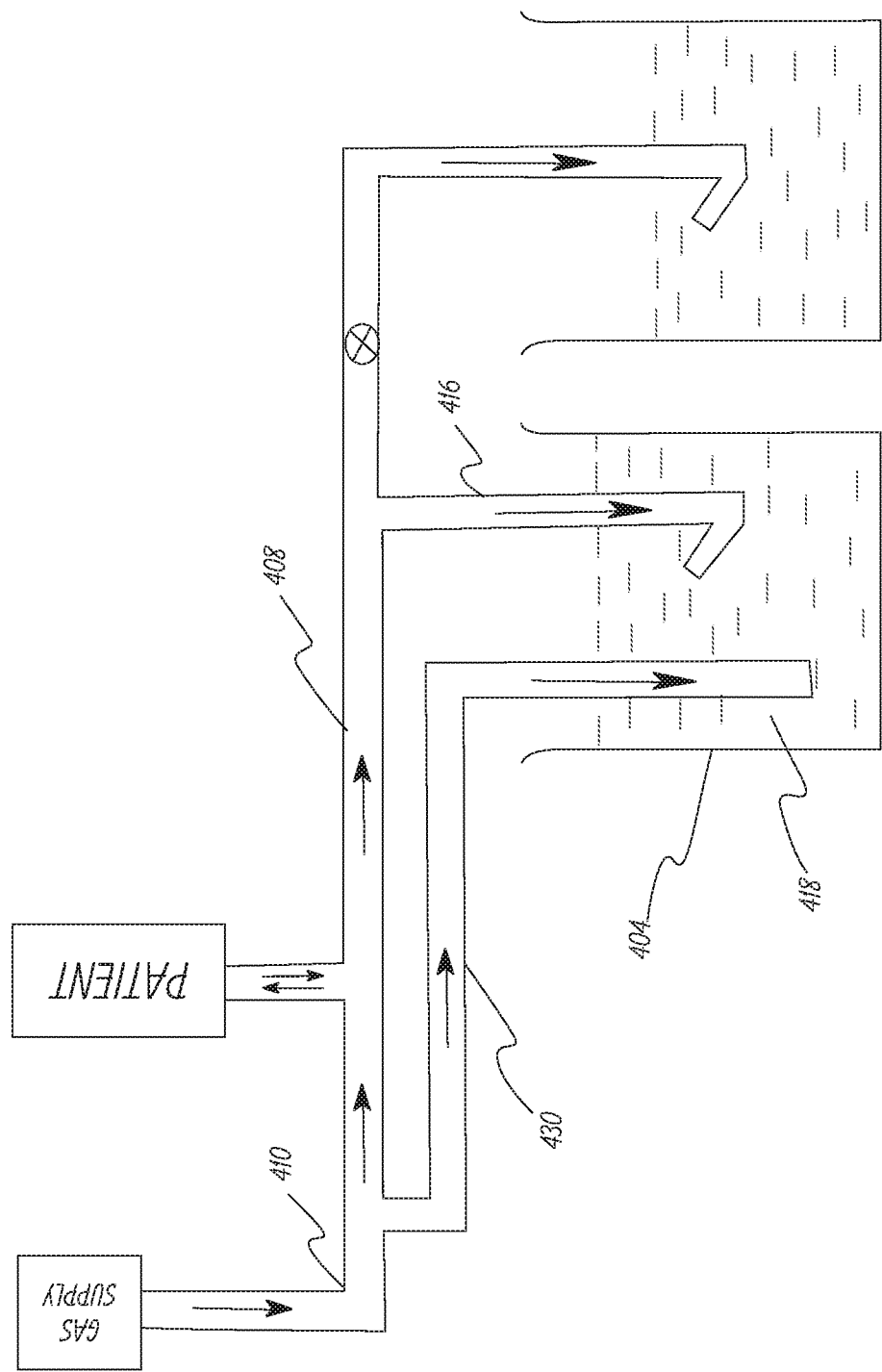
FIG. 4 depicts a ventilator system as shown in FIG. 2 with angled portions added to the peak inspiratory pressure control duct and the positive end-expiratory pressure control duct and one high pressure safety duct immersed in fluid in the first container at a depth greater than the immersed length of the peak inspiratory pressure control duct.

FIG. 4 illustrates a ventilator system similar to FIG. 3, but has in addition, at least one safety duct 430. The safety duct 430 is connected to the primary duct 408 near the proximal end 410 of the primary duct 408. The safety duct 430 is immersed in the body of fluid 418 in the first container 404 at depth greater than the immersed length of the peak inspiratory pressure control duct 416.

Figure 5:
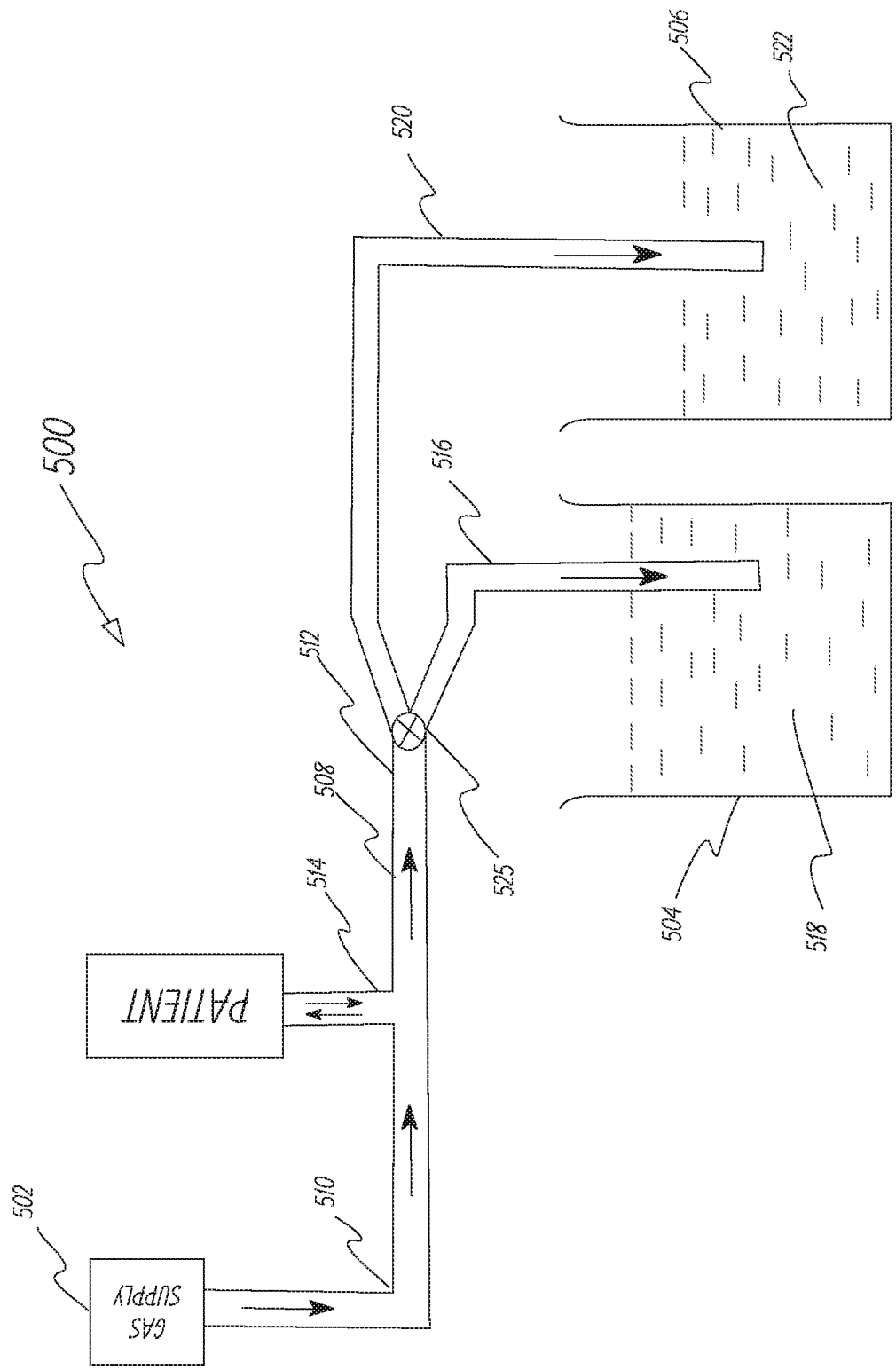
FIG. 5 depicts a ventilator system utilizing a peak inspiratory pressure control duct immersed in fluid in a first container; a positive end-expiratory pressure control duct immersed in fluid in a second container; one three-port valve connected to the peak inspiratory pressure control duct, the positive end-expiratory pressure control duct and a primary duct; and the height of the column of fluid in the first container is greater than the height of the column of fluid in the second container.

FIG. 5 illustrates a patient ventilator system 500 having a pressurized gas supply 502, two containers 504 and 506 filled with fluid, and a primary duct 508 with two ends—proximal end 510 and distal end 512. The proximal end 510 is connected to the pressurized gas supply 502. The primary duct 508 is adapted for connection to a patient interface 514 between the proximal end 510 and distal end 512. A three-port (also known as three-way) valve 525 is provided with one inlet port and two outlet ports. The distal end 512 is connected to the inlet port of the three-port valve 525. The first outlet port of the valve 525 is connected to at least one peak inspiratory pressure (PIP) control duct 516 that is immersed in a body of fluid 518 in the first container 504. The second outlet port of the valve 525 is connected to at least one positive end-expiratory pressure (PEEP) control duct 520 that is immersed in the body of fluid 522 in the second container 506. In one embodiment, the two containers 504 and 506 are of the same height measured from the bottom inner surface of the container to the top opening of the container, and the distal ends (tips) of the peak inspiratory pressure control duct 516 and the positive end-expiratory pressure control duct 520 are at same vertical distance from the bottom inner surfaces of the two containers 504 and 506 respectively. The level of fluid in the first container 504 is greater than the level of fluid in the second container 506 whereby immersed vertical length as measured from the top of the fluid surface to the tip of a pressure control duct is greater for the peak inspiratory pressure control duct 516 than for the positive end-expiratory pressure control duct 520. In other embodiment, the height of the container 504 is greater than the height of container 506. In yet another embodiment, the level of fluid in container 504 is about the same as the level of fluid in container 506.

The valve 525 cycles between the first outlet port and the second outlet port thereby continuously switching the flow of gas from the inlet port to the first outlet port and the inlet port to the second outlet port. Each cycle corresponds to one breath. In operation, when the gas flows from the inlet port to the first outlet port of valve 525, gas flows through PIP control duct 516, which is set in the container 504 with higher level of fluid than the container 506 having the PEEP control duct 520, thereby controlling the PIP in the circuit. When the gas flows from the inlet port to the second outlet port of valve 525, gas in the pressurized circuit flows through PEEP control duct 520, which is set in a container 506 with lower level of fluid than the container 504 having the PIP control duct 516, thereby lowering the pressure to PEEP and allowing the patient to exhale. The valve 525 can then cycle back to the first outlet port to allow the patient to receive PIP, and the cycle may be repeated. In this manner, a patient can receive peak inspiratory pressure and positive end expiratory pressure (Bi-PAP ventilation) or intermittent positive pressure ventilation (IPPV).

In one embodiment, rate of cycling (measured in cycles per minute) of the valve 525 is controlled using a controller (not shown) communicably connected to the valve. In another embodiment, controller allows user to set time T1 (Inspiratory Time) during which gas flows from the inlet port to the first outlet port and time T2 (Expiratory Time) during which gas flows from the inlet port to the second outlet port. In one embodiment, T1 is set as time in seconds. In another embodiment, T1 or T2 can be set as a fraction of cycle time or as a ratio of T1 and T2 such that the sum of T1 and T2 equals time of one cycle. Because the PIP control duct is connected to the first outlet port and the PEEP control duct is connected to the second outlet port, T1 is inspiratory time and T2 is expiratory time of a cycle or breath. In one embodiment, the expiratory time T2 is set to be greater than inspiratory time T1, and the ratio T2/T1 is greater than 1. The ratio of inspiratory time and expiratory time may be depicted as T1:T2 and the ratio shown as 1:N where, in one embodiment, N is a number greater than 1. In another embodiment, the controller does not allow the value of N to be less than 1. In another embodiment, breaths per minute (bpm) and inspiratory time (T1) in seconds are set by the user, and the controller calculates expiratory time (T2) in seconds using the formula T2=(60/bpm)−T1. In yet another embodiment, if the calculated expiratory time (T2) in seconds is less than the inspiratory time (T1) in seconds set by the user, the controller sets T1=T2=30/bpm. In another embodiment, controller allows the user to control the ratio of inspiratory time T1 to expiratory time T2 or have T1 fixed as percent of cycle time to maintain a desired inspiration time to expiration time ratio. For example, if T1 is set as 33% of cycle time, then T2 will be 67% of cycle time, giving T1:T2 ratio of 1:2. In another embodiment, the controller is integrated with the valve, with the control logic embedded in the valve. In one embodiment, the failure mode of the valve 525 is the open position to the second outlet port whereby the gas flow is directed to the PEEP control duct 520 and the pressure in the ventilator system is maintained at the baseline, i.e. lower level. In another embodiment, if the controller sets the cycling rate of the valve 525 as zero, the valve remains in the open position to the second outlet port whereby the gas flow is directed to the PEEP control duct 520 and the pressure in the ventilator system is maintained at the baseline i.e. lower level. In another embodiment, if power to the valve 525 is shut off, the valve remains in the open position to the second outlet port whereby the gas flow is directed to the PEEP control duct 520 and the pressure in the ventilator system is maintained at the baseline i.e. lower level. Thus the apparatus can be converted from Bi-PAP ventilation to bubble CPAP by simply shutting off power to the valve or setting cycling rate of the valve to zero.

Figure 6:
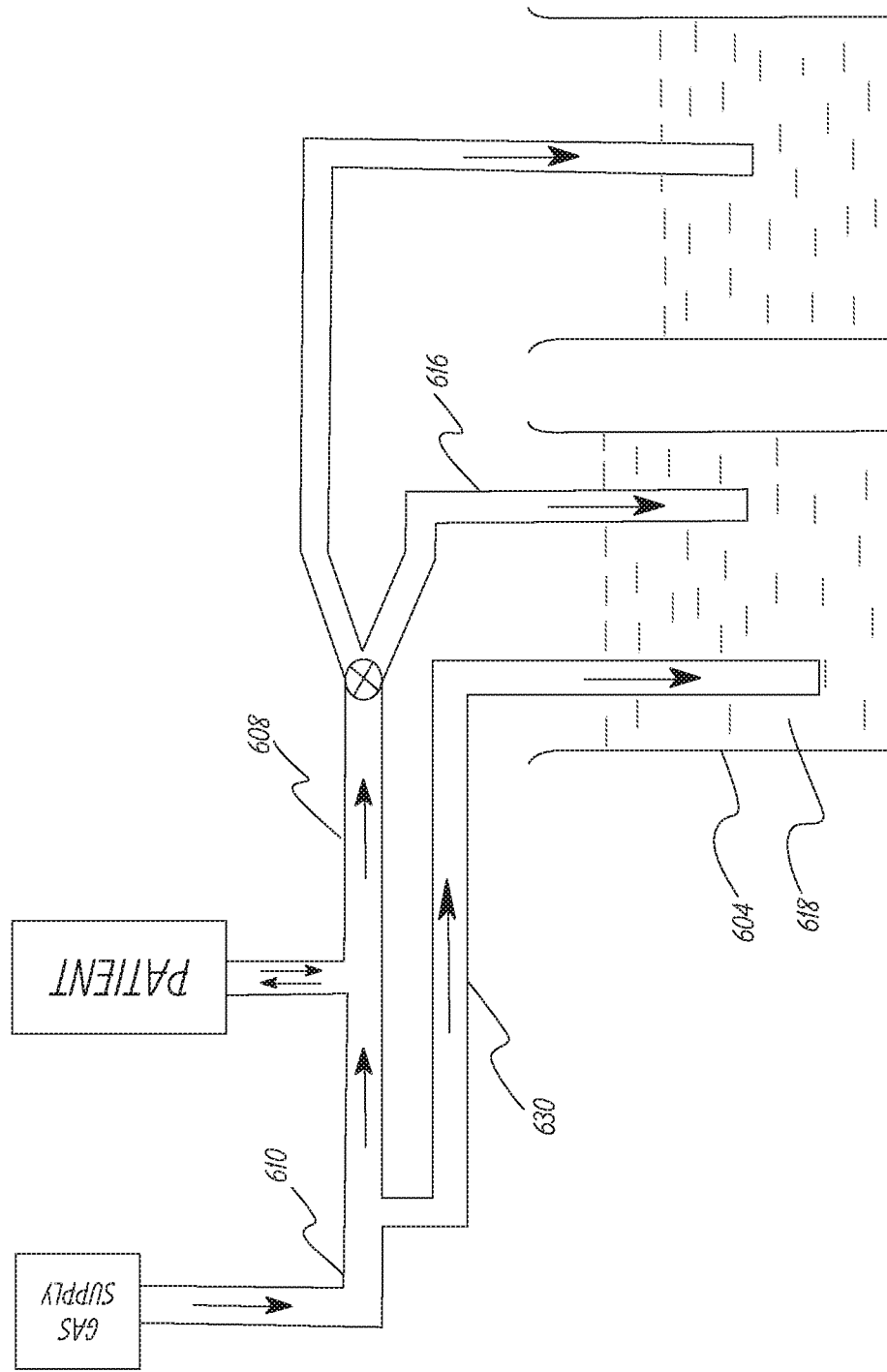
FIG. 6 depicts a ventilator system utilizing a peak inspiratory pressure control duct immersed in fluid in a first container; a positive end-expiratory pressure control duct immersed in fluid in a second container; one three-port valve connected to the peak inspiratory pressure control duct, the positive end-expiratory pressure control duct and a primary duct; one high pressure safety duct immersed in fluid in the first container at a depth greater than the immersed length of the peak inspiratory pressure control duct; and the height of the column of fluid in the first container is greater than the height of the column of fluid in the second container.

FIG. 6 illustrates a ventilator system similar to FIG. 5, but has in addition, at least one safety duct 630. The safety duct 630 is connected to the primary duct 608 near the proximal end 610 of the primary duct 608. The safety duct 630 is immersed in the body of fluid 618 in the first container 604 at depth greater than the immersed length of the peak inspiratory pressure control duct 616. The safety duct allows setting the limit of safe pressure relative to the set PIP pressure. For example, in some embodiments the fluid used is water, and the difference in vertical distance between the tip of the immersed safety duct 630 and the immersed PIP control duct 616 can be set at 5 cm if the user wants that the maximum pressure that the lungs may be subjected to not be greater than the set PIP pressure by 5 cm of water.

Figure 7:
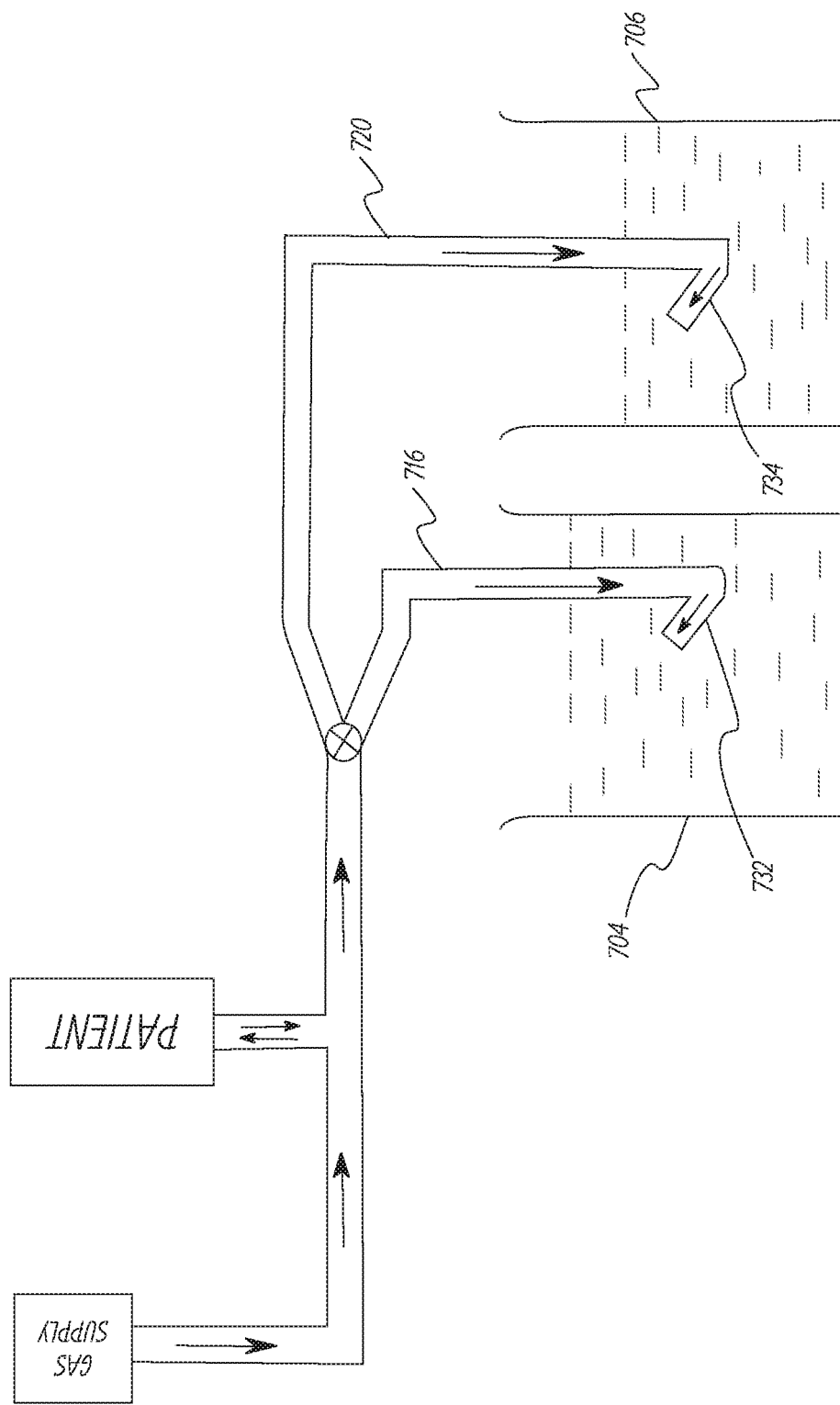
FIG. 7 depicts a ventilator system as shown in FIG. 5 with angled portions added to the peak inspiratory pressure control duct and to the positive end-expiratory pressure control duct.

FIG. 7 illustrates a patient ventilator system similar to that illustrated in FIG. 5 utilizing a PIP control duct 716 in the first container 704 and a PEEP control duct 720 in the second container 706. The ducts 716 and 720 are immersed in fluid and configured to modulate airway pressures in a patient receiving Bi-PAP or IPPV. The embodiment illustrated in FIG. 7 further comprises two angled sections 732 and 734 connected to the distal ends of the PIP and PEEP control ducts respectively. The angle of angled section may be altered between 0 and 180 degrees to the vertical to modify the amplitude and frequency of airway pressure oscillations that are superimposed on top of the airway pressure wave form for both the inhalation and exhalation cycles. In some embodiments, the angled arm of the angled section has length of between 2 cm and 10 cm. In some embodiments, more than two angled sections may be used. In other embodiments, the angles of the two or more angled sections may be substantially similar. In still other embodiments, the angles of the two or more angled sections may be different.

Figure 8:
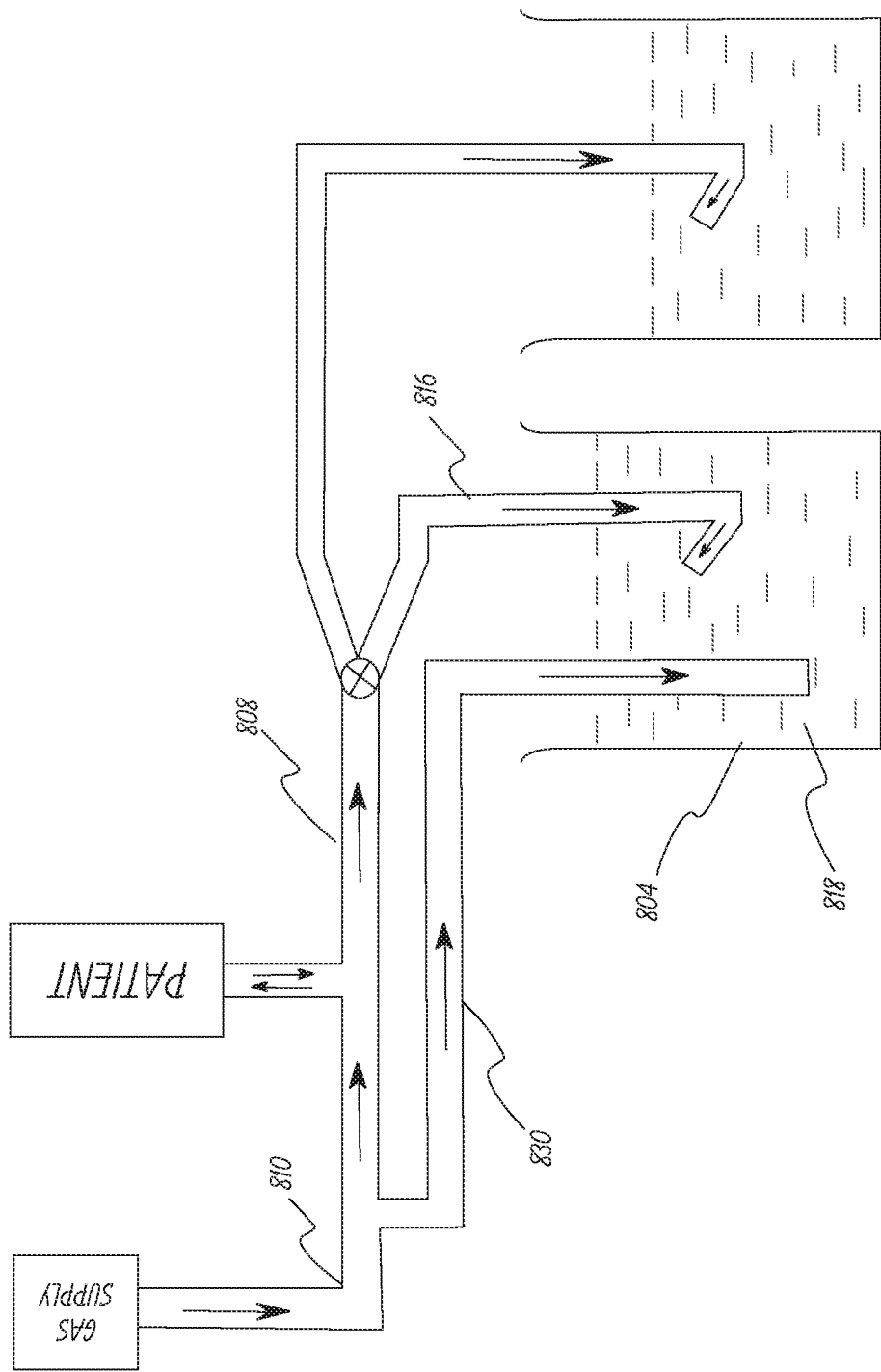
FIG. 8 depicts a ventilator system as shown in FIG. 6 with angled portions added to the peak inspiratory pressure control duct and to the positive end-expiratory pressure control duct and one high pressure safety duct immersed in fluid in the first container at a depth greater than the immersed length of the peak inspiratory pressure control duct.

FIG. 8 illustrates a ventilator system similar to FIG. 7, but has in addition, at least one safety duct 830. The safety duct 830 is connected to the primary duct 808 near the proximal end 810 of the primary duct 808. The safety duct 830 is immersed in the body of fluid 818 in the first container 804 at depth greater than the immersed length of the peak inspiratory pressure control duct 816.

Figure 9:
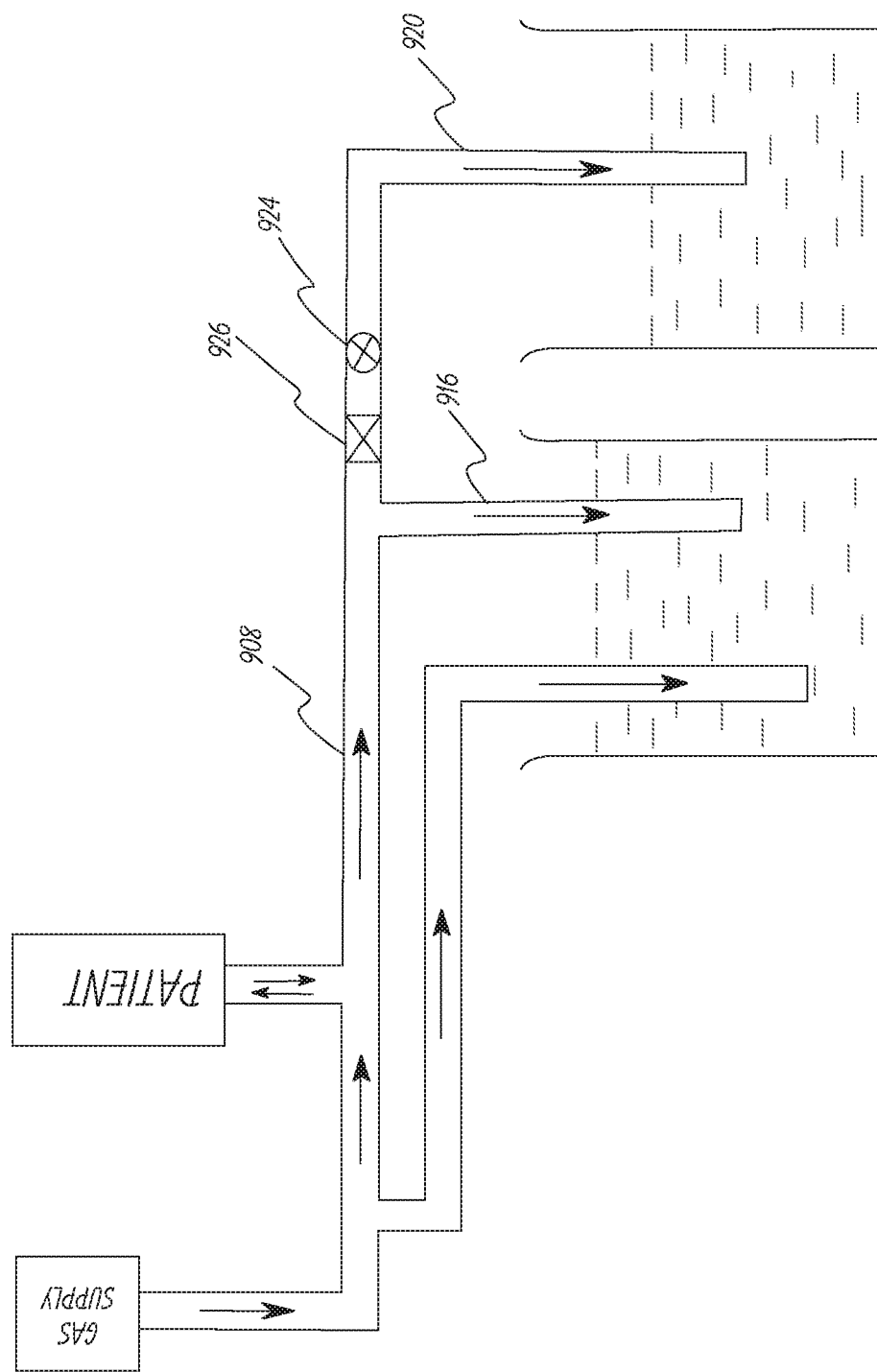
FIG. 9 depicts a ventilator system utilizing a peak inspiratory pressure control duct immersed in fluid in a first container; a positive end-expiratory pressure control duct immersed in fluid in a second container; a first valve that is a two-port valve located in-between the peak inspiratory pressure control duct and the positive end-expiratory pressure control duct; a second valve that is an on-off shutoff valve located in-between the peak inspiratory pressure control duct and the two-port valve; one high pressure safety duct immersed in fluid in the first container at a depth greater than the immersed length of the peak inspiratory pressure control duct; and the height of the column of fluid in the first container is greater than the height of the column of fluid in the second container.

FIG. 9 illustrates a ventilator system similar to that in FIG. 2, but has a second valve 926 as an additional safety. The second valve 926 is provided in between the peak inspiratory pressure control duct 916 and the two-port valve 924 wherein the second valve 926 is an open-shut type shutoff valve that can isolate the valve 924 and the positive end-expiratory pressure control duct 920 from the primary duct 908 and thereby from the remainder of the ventilator gas flow circuit. The isolation of the valve 924 may be necessary if there is a catastrophic failure of the valve 924. The shutting of the shutoff valve 926 also allows the user to employ the ventilator system as a bubble CPAP system.

In addition to the safety duct illustrated in FIGS. 2, 4 and 6, some embodiments can include additional safety features (not shown) such as a high pressure "pop-off" or "pop-open" safety valve to protect the patient from receiving airway pressures greater than a pre-determined threshold to reduce the likelihood of high pressures reaching the patient in the unlikely event that the patient circuit is occluded between the patient and the gas exiting the system through the fluid container. The pop-off valve provides a second level of protection when the safety duct such as duct 230 in FIG. 2 is present in the ventilator system. The pressure level setting of pop-off valve will be generally higher than the blow-out pressure setting of the safety duct. Note however that pop-off safety valve is generally pre-set to certain values and does not provide user the flexibility provided by the safety duct, which allows setting the limit of safe pressure relative to the set PIP pressure.

Figure 10:
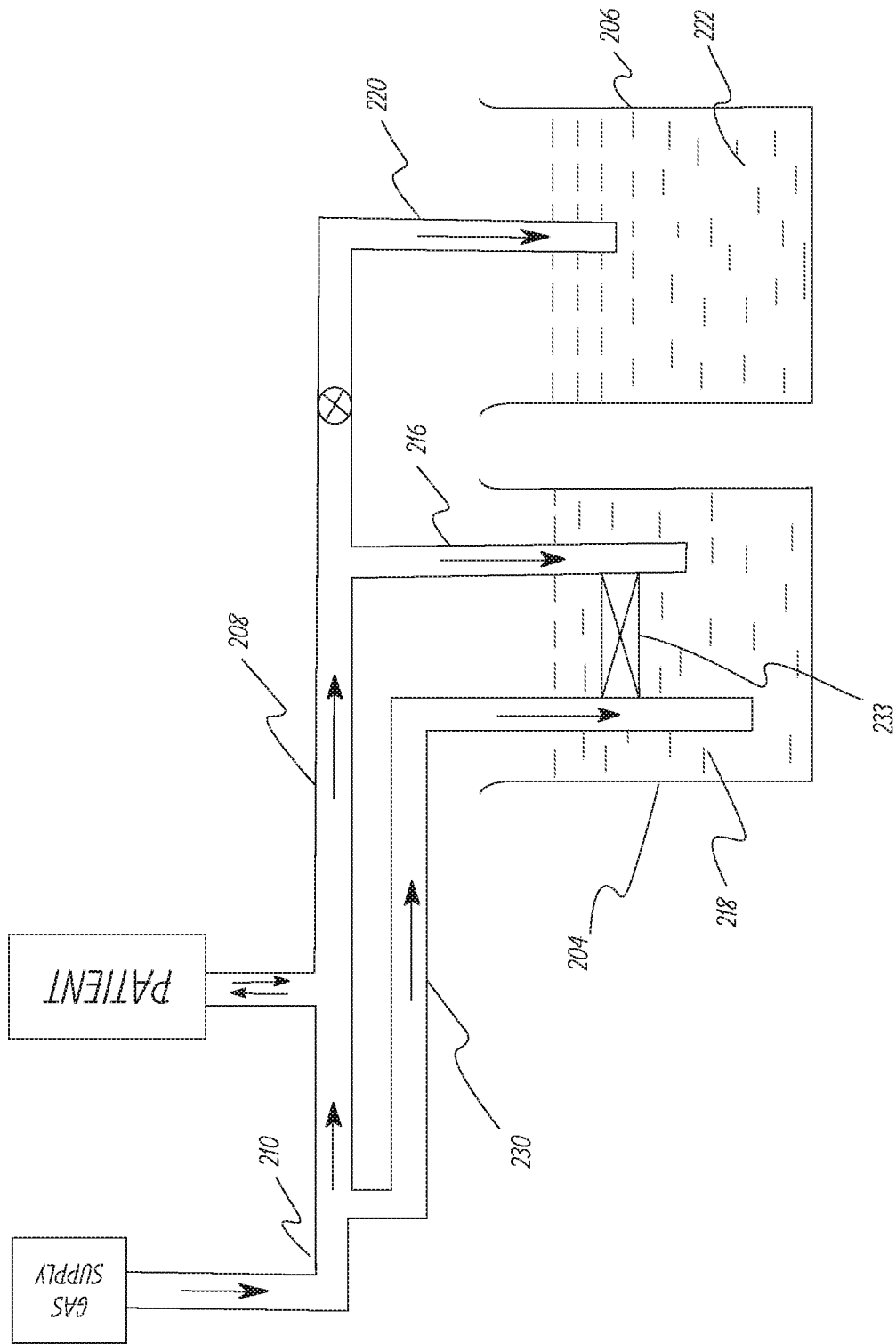
FIG. 10 depicts a ventilator system utilizing a connector to interconnect the peak inspiratory pressure control duct with the high-pressure safety duct.

In an embodiment shown in FIG. 10, which illustrates a ventilator system similar to that in FIG. 2, the safety duct 230 is interconnected using connector 233 with the PIP control duct 216 whereby the user can adjust the vertical spacing between the tip of the PIP control duct 216 and the tip of the safety duct 230 by sliding the connector or in incremental steps of the connector, thereby providing safety of a measured fluid column height above the PIP pressure for blow out of pressurized gas in case of a pressure surge in the ventilator system. In certain embodiments, the fluid is water and the user can adjust the tip of the safety duct 230 relative to the tip of the PIP control duct 216 such that the high pressure limit (pop off) is in the range of 0 to about 15 cm water column above the PIP pressure. In the embodiment shown in FIG. 10, the level of fluid 218 in container 204 is about the same as the level of fluid 222 in container 206, but the levels of fluid in the two containers could also be different as shown in the embodiments described before. In certain embodiments as shown in FIG. 10, the distal ends (tips) of the peak inspiratory pressure control duct 216 and the positive end-expiratory pressure control duct 220 are at different vertical distances from the bottom inner surfaces of the two containers 204 and 206, respectively.

Some embodiments can include a low-pressure "pop-open" or one-way valve (not shown) to protect the patient from receiving airway pressures lower than a pre-determined threshold, for example sub-atmospheric pressures. In this manner, the one-way valve can help prevent a lung from collapsing, help prevent the patient from inhaling fluid, and help prevent the patient from re-breathing exhaled gases. Fresh gas of controlled concentration (not shown) can also be supplied to the one-way valve.

Figure 11:
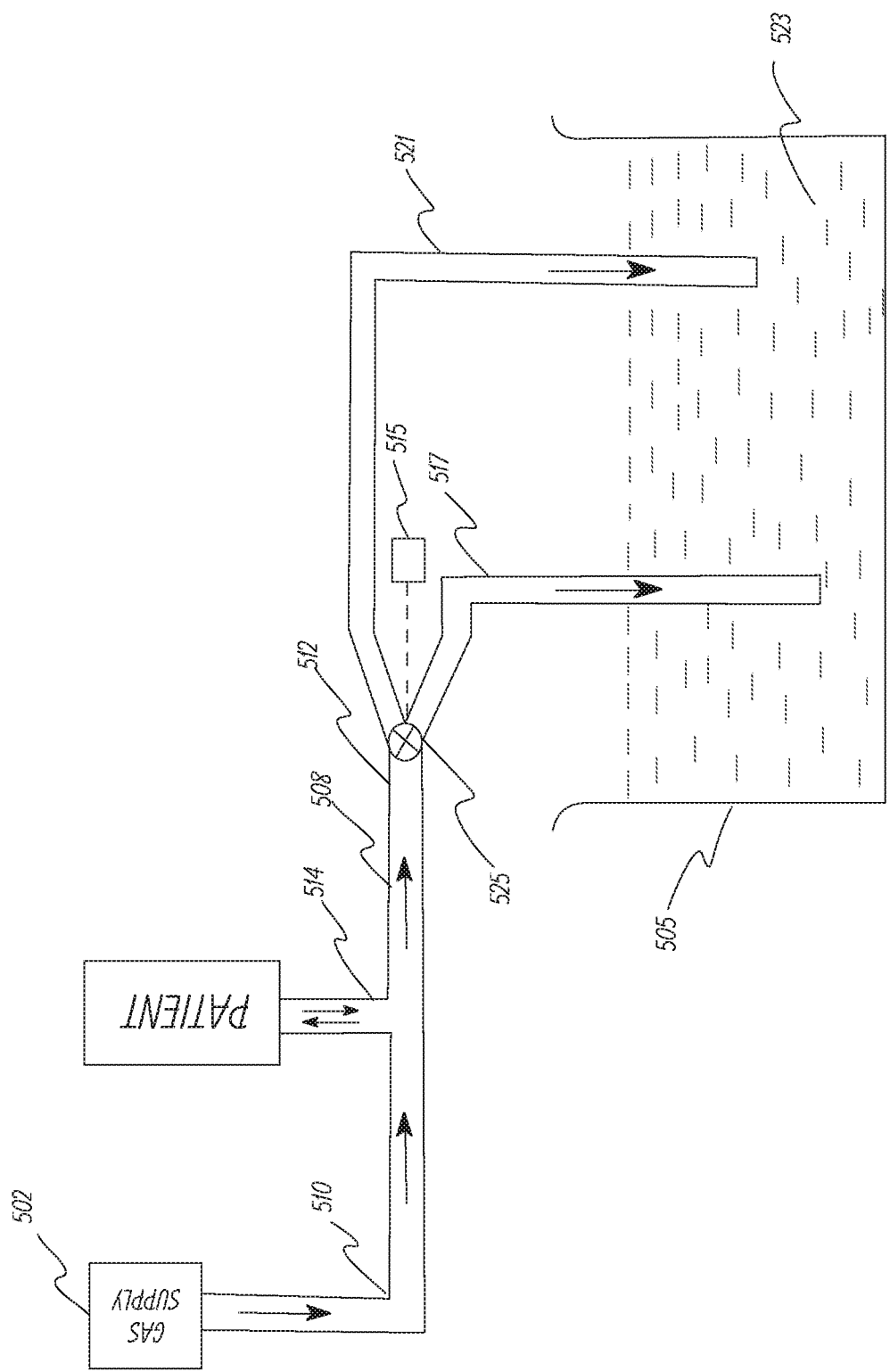
FIG. 11 depicts a ventilator system utilizing a peak inspiratory pressure control duct immersed in fluid in a container; a positive end-expiratory pressure control duct immersed in fluid in the same container; one three-port valve connected to the peak inspiratory pressure control duct, the positive end-expiratory pressure control duct and a primary duct; a controller communicably connected to the valve; and immersed length of the peak inspiratory pressure control duct is greater than immersed length of the positive end-expiratory pressure control duct.

FIG. 11 illustrates a patient ventilator system having a pressurized gas supply 502, a container 505 filled with fluid, and a primary duct 508 with two ends—the proximal end 510 and the distal end 512. The proximal end 510 is connected to the pressurized gas supply 502. The primary duct 508 is adapted for connection to a patient interface 514 between the proximal end 510 and distal end 512. A three-port (also known as three-way) valve 525 is provided with one inlet port and two outlet ports. The distal end 512 is connected to the inlet port of the three-port valve 525. The first outlet port of the valve 525 is connected to at least one peak inspiratory pressure (PIP) control duct 517 that is immersed in a body of fluid 523 in the container 505. The second outlet port of the valve 525 is connected to at least one positive end-expiratory pressure (PEEP) control duct 521 that is immersed in the body of fluid 523 in the container 505. The immersed vertical length as measured from the top of the fluid surface to the tip of a pressure control duct is greater for the PIP control duct 517 than for the PEEP control duct 521. The valve 525 cycles between the first outlet port and the second outlet port thereby continuously switching the flow of gas from the inlet port to the first outlet port and the inlet port to the second outlet port. Each cycle corresponds to one breath. In one embodiment, rate of cycling (measured in cycles per minute) of the valve 525 is controlled using a controller 515 communicably connected to the valve. In another embodiment, controller 515 allows user to set time T1 during which gas flows from the inlet port to the first outlet port and time T2 during which gas flows from the inlet port to the second outlet port. In one embodiment, T1 is set as time in seconds. In another embodiment, T1 or T2 can be set as a fraction of cycle time or as a ratio of T1 and T2 such that the sum of T1 and T2 equals time of one cycle. Because the PIP control duct is connected to the first outlet port and the PEEP control duct is connected to the second outlet port, T1 is inspiratory time and T2 is expiratory time of a breath. In one embodiment, the expiratory time T2 is set to be greater than inspiratory time T1. In another embodiment, breaths per minute (bpm) and inspiratory time T1 in seconds are set by the user, and the controller calculates expiratory time T2 in seconds using the formula T2=(60/bpm)−T1. In yet another embodiment, if the calculated expiratory time T2 in seconds is less than the inspiratory time T1 in seconds set by the user, the controller 515 sets T1=T2=30/bpm. In another embodiment, controller 515 allows user to control the ratio of inspiratory time T1 to expiratory time T2 or have T1 fixed as percent of cycle time to maintain a desired inspiration time to expiration time ratio. In another embodiment, the controller 515 is integrated with the valve, with the control logic embedded in the valve. In one embodiment, the failure mode of the valve 525 is the open position to the second outlet port whereby the gas flow is directed to the PEEP control duct 520 and the pressure in the ventilator system is maintained at the baseline i.e. lower level. In another embodiment, if the controller 515 sets the cycling rate of the valve 525 as zero, the valve remains in the open position to the second outlet port whereby the gas flow is directed to the PEEP control duct 520 and the pressure in the ventilator system is maintained at the baseline, i.e. lower level. In another embodiment, if power to the valve 525 or the controller 515 is switched off, the valve remains in the open position to the second outlet port whereby the gas flow is directed to the PEEP control duct 520 and the pressure in the ventilator system is maintained at the baseline, i.e. lower level.

Figure 12:
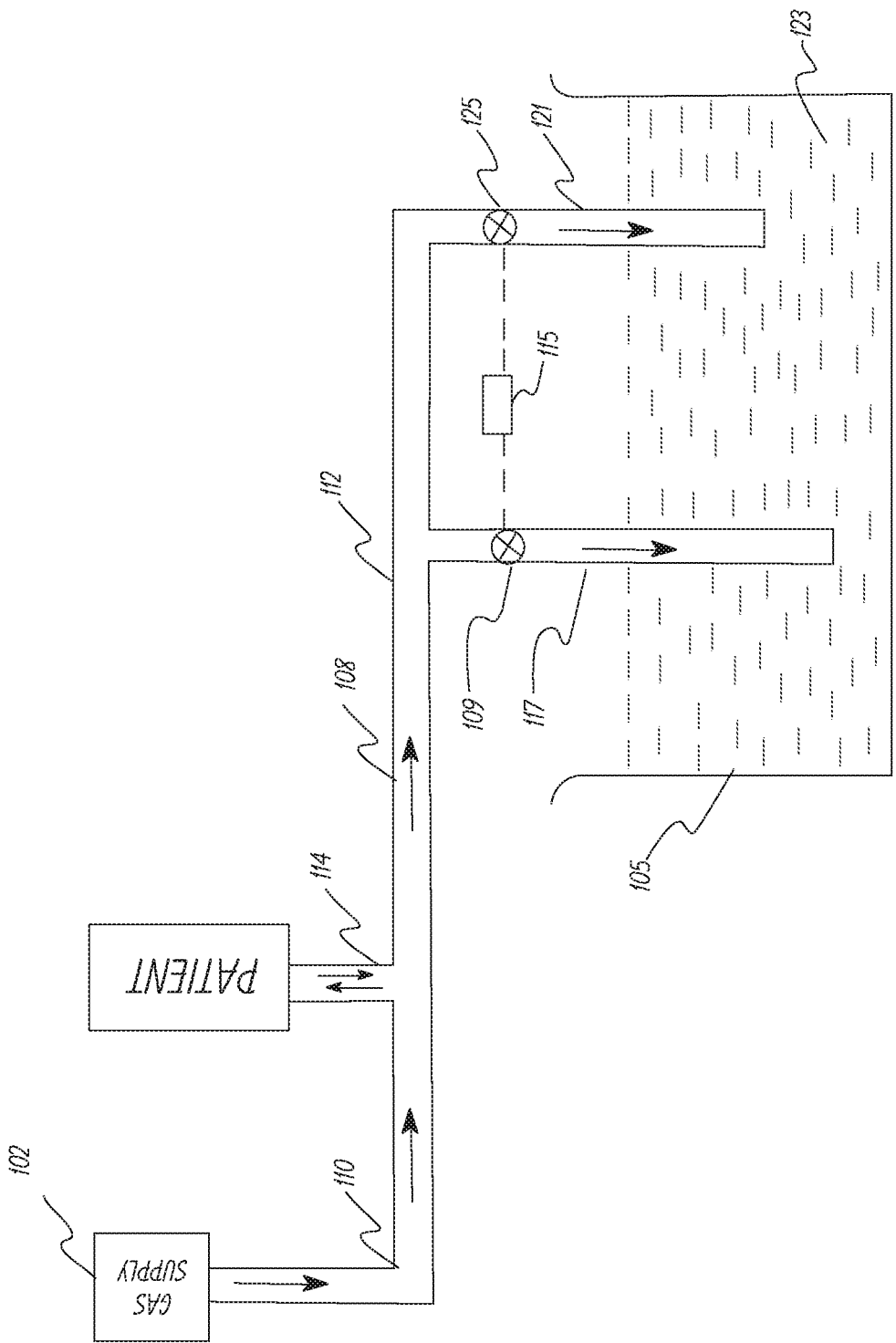
FIG. 12 depicts a ventilator system utilizing a peak inspiratory pressure control duct immersed in fluid in a container; a positive end-expiratory pressure control duct immersed in fluid in the same container; one two-port valve located on the positive end-expiratory pressure control duct; one two-port valve located on the peak inspiratory pressure control duct; a controller communicably connected to both the valves; and immersed length of the peak inspiratory pressure control duct is greater than immersed length of the positive end-expiratory pressure control duct.

FIG. 12 illustrates a patient ventilation system having a pressurized gas supply 102, a container 105 filled with fluid, and a primary duct 108 with two ends—the proximal end 110 and the distal end 112. The proximal end 110 is connected to the pressurized gas supply 102. The duct 108 is adapted for connection to a patient interface 114 between the proximal end 110 and distal end 112. At the distal end 112, at least one peak inspiratory pressure (PIP) control duct 117 is connected and immersed in a body of fluid 123 in the container 105. At least one positive end-expiratory pressure (PEEP) control duct 121 is also connected to the distal end 112 of the duct and immersed in the body of fluid 123 in the container 105. The immersed length of the PIP control duct 117 is greater than the immersed length of the PEEP control duct 121. A two-port valve 109 is placed on the PIP control duct 117 and is located between the PIP control duct 117 and the distal end 112 of the primary duct. Another two-port valve 125 is placed on the PEEP control duct 121 and is located between the PEEP control duct 121 and the distal end 112 of the primary duct. The valves 109 and 125 cycle from open to shut position and back to open position, and the rate of cycling of the valves can be controlled by a controller 115 communicably connected to the valves 109 and 125. The valves 109 and 125 are controlled by the controller 115 such that when the valve 109 is open, the valve 125 is closed and when the valve 109 is closed, the valve 125 is open.

In operation, when the two-port valve 125 is open and the two-port valve 109 is closed, gases flow through PEEP control duct 121, thereby controlling the PEEP in the circuit. When the two-port valve 125 is closed and the two-port valve 109 is open, gases in the pressurized circuit flows through PIP control duct 117, thereby raising the pressure to peak inspiratory pressure. The valve 125 can then be opened again and valve 109 closed to allow the patient to exhale, and the process may be repeated. In this manner, a patient can receive peak inspiratory pressure and positive end expiratory pressure (Bi-PAP ventilation) or intermittent positive pressure ventilation (IPPV).

More embodiments concern methods of using one or more of the aforementioned combinations to assist the breathing of a subject (e.g., an adult, child, infant human being or another mammal). By some approaches, a subject having breathing problems is identified or selected and said subject is connected to one or more of the devices described herein. In some embodiments the subject is attached to the device by nasal prongs and in other embodiments, the subject is attached to the device by face or nasal masks, tube(s) placed in the nasopharynx, endotracheal tubes, tracheostomy tubes, or combinations thereof. Once the subject and device are connected, gas flow is initiated. Preferable gas flows for infants are about 1 to 10 L/min, whereas adults may require gas flows of about 1 to 30 L/min and large mammals may require 1 to 100 L/min or more. Optionally, the frequency, amplitude of cycling pressure, or volume of gas delivered is monitored so as to adjust the breathing assistance for the particular subject. In some embodiments, a device having a particular immersed length of the peak inspiratory pressure duct, immersed length of the positive end-expiratory pressure duct, diameter or cross-sectional area of PIP and PEEP control ducts, or particular fluid can be selected for a subject's unique needs. That is, in some embodiments, a patient in need of breathing assistance is selected or identified and a breathing assistance device, as described herein, is selected or identified according to a subject's age, size, or therapeutic need.

Some embodiments include a method for providing continuous positive airway pressure with oscillating positive end-expiratory pressure to a subject by providing any of the devices or apparatuses described herein, releasing gas from the gas supply into the apparatus and delivering the gas to the subject. Other embodiments include a method for increasing the volume of gas delivered to a subject by providing any of the breathing assistance devices or apparatuses described herein, adjusting the angle of the distal end of the duct with respect to a vertical axis and releasing gas from the gas supply into the apparatus to deliver gas to the subject. In some embodiments, the distal end of the duct is adjusted to an angle greater than or equal to between about 91-170 degrees. In other embodiments, the distal end of the duct is adjusted to an angle of about 135 degrees with respect to a vertical axis.

Example 1

This example describes the ventilator system used and experiments performed to test the system described in FIG. 1. A lung machine manufactured by Ingmar Medical, Pittsburgh, Pa. (www.ingmarmed.com) was connected at patient interface of the ventilator system. A two-port (two-way) solenoid valve manufactured by MAC Valves, Inc., Wixom, Mich. (www.macvalves.com) was used in the system. The open-shut cycle of the valve was controlled using an electronic timer made by IDEC Corporation, Sunnyvale, Calif. (us.idec.com). Compressed air and air/oxygen mixtures were used in the tests. The tubing used was the standard 10 mm tubing used with conventional ventilator systems in a hospital setting. The fluid in the containers was water at room temperature. The pressure at the patient interface was measured using a manometer manufactured by Life Design Systems, Inc., Madison, Wis. The manometer had a range of −20 cm water to +80 cm water in increments of 1 cm water. Tests were run for gas flow rates from 0.5 L/min through 5 L/min in increments of 0.5 L/min, and from 5 L/min through 15 L/min in increments of 1 L/min. The gas flow rate was set using flowmeter manufactured by Precision Medical, Northampton, Pa. (www.precisionmedical.com). The immersed length of the PIP control duct was varied from 10 to 30 cm of water, and the immersed length of the PEEP control duct was varied from 2 to 10 cm of water. The cycling of the valve was done from 1 cycle per minute to 60 cycles per minute. Each cycle corresponds to a breath and thus the tests were conducted from 1 breath per minute to 60 breaths per minute.

The valve offers a resistance to flow of gas, resulting in a loss of pressure. The loss of pressure due to the resistance of valve increased as the flow rate of gas was increased. At gas flow rates of 15 L/min, a pressure loss as high as 4 cm water was observed in the valve, resulting in a back pressure whereby observed PEEP at patient interface was about 4 cm of water higher than that set by the PEEP control duct in the second container. Because the PIP control duct did not have a valve in the line of flow from the patient interface to the PIP control duct, the PIP setting did not experience the back pressure from the valve. Therefore, depending on the flow rate of gas, a correction to account for the back pressure of the valve had to be made to the PEEP control duct. When the back pressure was 4 cm of water, a correction of 4 cm to the immersed length of the PEEP control duct in the second container was made such that actual immersed length was 4 cm less than the required PEEP at the patient interface. Thus if the required PEEP at the patient interface is 10 cm of water and the back pressure is 4 cm of water, then immersed length of PEEP control duct is 6 cm.

For comparison, tests were also conducted using a single container containing water wherein both the PIP and PEEP control ducts were immersed in one and the same container, as disclosed in U.S. Pat. No. 8,499,759, and the disclosure of U.S. Pat. No. 8,499,759 is incorporated herein by reference in its entirety. The bubbles from one duct had an impact on observed pressure from the other duct when the PIP and PEEP control ducts were in the same container. This impact was more pronounced at higher gas flow rates and less pronounced when the diameter of the container was increased. It was found that all other conditions remaining the same, the observed pressure at the patient interface was closer to the pressure set by the control ducts when the two control ducts were in different containers (as in FIG. 1) compared with the observed pressures when the control ducts were in the same container (as in U.S. Pat. No. 8,499,759). Further, it was found that, for a given gas flow rate, correction to account for back pressure in PEEP control duct is similar whether the two control ducts were placed in one container or in two separate containers.

Example 2

The system in Example 1 was modified to include a safety duct as shown in FIG. 2. The safety duct was set at a pressure 3 cm of water above the PIP pressure. The primary duct was intentionally squeezed at the distal end to simulate occlusion of the duct and the safety duct released the pressure buildup when the pressure at the patient interface reached 3 cm of water above the PIP pressure. The tests were repeated successfully at different pressure levels.

Example 3

This example describes the ventilator system used and experiments performed to test the system described in FIG.

5. A lung machine manufactured by Ingmar Medical, Pittsburgh, Pa. (www.ingmarmed.com) was connected at patient interface of the ventilator system. A three-port (three-way) solenoid valve manufactured by MAC Valves, Inc., Wixom, Mich. (www.macvalves.com) was used in the system. The size of the three-port valve was the same as the two-port (two-way) valve used in Example 1. The cycling of the valve was controlled using an electronic timer made by IDEC Corporation, Sunnyvale, Calif. (us.idec.com). Compressed air and air/oxygen mixtures were used in the tests. The tubing used was the standard 10 mm plastic tubing used with conventional ventilator systems in a hospital setting. The fluids in the containers were water at room temperature. The pressure at the patient interface was measured using a manometer manufactured by Life Design Systems, Inc., Madison, Wis. The manometer had a range of −20 cm of water to +80 cm of water in increments of 1 cm water. Tests were run for gas flow rates from 0.5 L/min through 5 L/min in increments of 0.5 L/min, and from 5 L/min through 15 L/min in increments of 1 L/min. The gas flow rate was set using flowmeter manufactured by Precision Medical, Northampton, Pa. (www.precisionmedical.com). The immersed length of the PIP control duct was varied from 10 to 30 cm of water, and the immersed length of the PEEP control duct was varied from 2 to 10 cm of water. The cycling of the valve was done from 1 cycle per minute to 60 cycles per minute. Each cycle corresponds to a breath and thus the tests were conducted from 1 breath per minute to 60 breaths per minute.

Similar to the back pressures observed in Example 1, at gas flow rates of 15 L/min, a back pressure as high as 4 cm. of water was observed in the valve. But unlike the performance observed for the system in FIG. 1 of Example 1 wherein the PEEP at the patient interface was affected by back pressure but the PIP at patient interface was not affected by back pressure, the three-port valve resulted in back pressure that affected similarly both PIP and PEEP as observed at the patient interface. Both the PIP control duct and the PEEP control duct had the three-port valve in the line of flow from the patient interface to respective control ducts, whereby correction to account for back pressure of the valve had to be made to both the PEEP control duct and the PIP control duct. For a given gas flow rate, the correction was similar for both the PIP control duct and the PEEP control duct. When the back pressure was 4 cm of water, a correction of 4 cm to the immersed length of the PEEP control duct was made such that actual immersed length of the PEEP control duct was 4 cm less than the required PEEP at the patient interface. And similarly a correction of 4 cm to immersed length of the PIP control duct was made such that actual immersed length of the PIP control duct was 4 cm less than the required PIP at the patient interface. Thus if the required PEEP at the patient interface is 10 cm of water, the required PIP at the patient interface is 30 cm of water, and the back pressure is 4 cm of water, then the immersed length of PEEP control duct is 6 cm and the immersed length of the PIP control duct is 26 cm. A chart was prepared that showed relationship between flow rate of gas in L/min and correction in cm. of water.

The back pressure from the valve is primarily due to size the valve (e.g., diameter of valve orifice through which gas passes, diameter of inlet and outlet passage ways and ports of valve) that creates resistance to flow of gas. The smaller the orifice size, e.g., smaller the diameter, the higher the resistance. To minimize the back pressure and the resulting correction to immersed length of PIP control duct and PEEP control duct, the size of orifice, the size of internal passage ways, the size of the ports are preferably the same as or similar to the size of the ventilator tubing. The pressure loss in the valve can be calculated using a coefficient of flow (Cv) of the valve. The calculation method is generally known. The pressure loss decreases as the Cv value increases. The gas is a compressible fluid and the Cv value and pressure loss of gas depends on temperature and pressure of the gas. The pressure of the gas in the ventilator system is slightly above atmospheric (2-50 cm of water above atmospheric) and the temperature of the gas in the ventilator system may be kept slightly above room temperature and could be as high as 40 degrees Celsius. For the gas pressure and temperature that are generally prevalent in a ventilator system, the coefficient of flow Cv of the valve is preferably greater than about 1.5 and more preferably greater than about 2.

Example 4

Tests were conducted using the valve, timer and tubing system of Example 3, but using a single container containing water wherein both the PIP control duct and the PEEP control duct were immersed in water as shown in FIG. 11. The test parameters such as gas flow rates, immersed lengths of PIP and PEEP control ducts, cycling rates of valve were same as those in Example 3. The bubbles from one duct had an impact on observed pressure from the other duct when the PIP control duct and the PEEP control duct were in the same container. The impact was more pronounced at higher gas flow rates and less pronounced when the diameter of the container was increased. It was found that, all other conditions remaining the same, the observed pressure at the patient interface was closer to the pressure set by the control ducts when the two control ducts were in different containers compared with the observed pressures when the control ducts were in the same container. When back pressures in Example 3 were compared with back pressures in Example 4, it was found that, for a given gas flow rate, correction to account for back pressure is similar for both PIP control duct and PEEP control duct irrespective of whether the two control ducts were placed in one container or in two separate containers.

Example 5

This example describes the ventilator system used and tests performed using a system as shown in FIG. 12 wherein two two-port valves were used to determine whether two two-port valves would replicate the system and tests done in Example 4 where a single three-port valve was used. Two two-port solenoid valves manufactured by MAC Valves, Inc., Wixom, Mich. were used in the system. The first two-port solenoid valve was placed on the PIP control duct and is located between the PIP control duct and the distal end of the primary duct. The second two-port solenoid valve was placed on the PEEP control duct and is located between the PEEP control duct and the distal end of the primary duct. The test parameters were the same as those in Examples 3 and 4. The two valves were controlled such that when the first valve was open, the second valve was closed and when the first valve was closed, the second valve was open. The two two-port valves were identical and their size including valve aperture and port diameters was the same as that of the three-port valve used in Example 4. The observed performance of the system in Example 5 was similar to the performance of the system in Example 4. Unlike in Example 1 where a single two-port valve is used and correction to account for back pressure was greater than zero for the PEEP control duct and zero for the PIP control duct, in Example 5 the back pressure correction was found to be greater than zero and similar for both the PIP control duct and the PEEP control duct.

It will be appreciated that several of the above-disclosed and other features and functions, or alternatives or varieties thereof, may be desirably combined into many other different systems or applications. Also that various alternatives, modifications, variations or improvements therein may be subsequently made by those skilled in the art which are also intended to be encompassed by the following claims.

In the description above, for the purposes of explanation, numerous specific requirements and several specific details have been set forth in order to provide a thorough understanding of the embodiments. It will be apparent however, to one skilled in the art, that one or more other embodiments may be practiced without some of these specific details. The particular embodiments described are not provided to limit the invention, but to illustrate it. The scope of the invention is not to be determined by the specific examples provided above, but only by the claims below. In other instances, well-known structures, devices, and operations have been shown in block diagram form or without detail in order to avoid obscuring the understanding of the description. Where considered appropriate, reference numerals or terminal portions of reference numerals have been repeated among the figures to indicate corresponding or analogous elements, which may optionally have similar characteristics.

It should also be appreciated that reference throughout this specification to "one embodiment", "an embodiment", "one or more embodiments", or "different embodiments", for example, means that a particular feature may be included in the practice of the invention. Similarly, it should be appreciated that in the description various features are sometimes grouped together in a single embodiment, figure, or description thereof for the purpose of streamlining the disclosure and aiding in the understanding of various inventive aspects. This method of disclosure, however, is not to be interpreted as reflecting an intention that the invention requires more features than are expressly recited in each claim. Rather, as the following claims reflect, inventive aspects may lie in less than all features of a single disclosed embodiment. In another situation, an inventive aspect may include a combination of embodiments described herein or in a combination of less than all aspects described in a combination of embodiments. Thus, the claims following the Detailed Description are hereby expressly incorporated into this Detailed Description, with each claim standing on its own as a separate embodiment of the invention.

The invention claimed is:

1. An apparatus to provide breathing support to a patient comprising:
    a valve comprising at least three ports, said three ports comprising an inlet port, a first outlet port and a second outlet port, the inlet port adapted for connection to a patient interface via a primary duct configured for a flow of a gas;
    at least one peak inspiratory pressure (PIP) control duct connected to the first outlet port of the valve;
    at least one positive end-expiratory pressure (PEEP) control duct connected to the second outlet port of the valve;
    a container containing a first body of fluid, wherein the PIP control duct and the PEEP control duct are configured to be immersed in the first body of fluid in the container, and an immersed length of the PIP control duct is greater than an immersed length of the PEEP control duct;
    at least one safety duct adapted for connection to the primary duct and configured to be immersed in the first body of fluid, wherein an immersed length of the safety duct is greater than the immersed length of the PIP control duct;
    wherein the valve is configured to cycle between the first outlet port and the second outlet port thereby switching the flow of the gas from the inlet port to only the first outlet port and from the inlet port to only the second outlet port;
    wherein a cycle corresponds to one breath; and
    wherein when the gas flows from the inlet port to the first outlet port of the valve, the gas flows through the PIP control duct, thereby controlling a PIP in the apparatus so that the patient receives the PIP, and when the gas flows from the inlet port to the second outlet port of the valve, the gas in the apparatus flows through the PEEP control duct, thereby lowering pressure in the apparatus to a PEEP so that the patient receives the PEEP.

2. The apparatus of claim 1, wherein the valve is a solenoid valve and has a coefficient of flow Cv greater than about 1.5.

3. The apparatus of claim 1, further comprising at least one controller communicably connected to the valve to control a rate of cycling of the valve, thereby controlling a number of breaths per minute, and to control at least one of (a) an inspiratory time in seconds, (b) a ratio of the inspiratory time to an expiratory time, and (c) the inspiratory time as a percentage of a cycle time, thereby maintaining the ratio of the inspiratory time to the expiratory time as determined by a user.

4. The apparatus of claim 1, wherein the valve is a solenoid valve.

5. The apparatus of claim 1, wherein the fluid comprises water.

6. The apparatus of claim 1, wherein at least one angled section is connected to a tip of at least one of the PIP control duct and the PEEP control duct.

7. The apparatus of claim 1, further comprising a pressurized gas supply.

8. An apparatus to provide breathing support to a patient comprising:
    a pressurized gas supply;
    at least one body of fluid;
    a primary duct including proximal and distal ends, the proximal end adapted for connection to the pressurized gas supply, the primary duct also adapted for connection to a patient interface between the proximal and distal ends;
    a valve comprising at least three ports, said three ports comprising one inlet port, a first outlet port and a second outlet port, the inlet port adapted for connection to the distal end of the primary duct;
    wherein the apparatus further comprises:
    (i) at least one peak inspiratory pressure (PIP) control duct connected to the first outlet port of the valve and configured to be immersed in the at least one body of fluid;
    (ii) at least one positive end-expiratory pressure (PEEP) control duct connected to the second outlet port of the valve and configured to be immersed in the at least one body of fluid; and (iii) wherein an immersed length of the PIP control duct is greater than an immersed length of the PEEP control duct;

(iv) at least one safety duct adapted for connection to the primary duct and configured to be immersed in the at least one body of fluid, wherein an immersed length of the safety duct is greater than the immersed length of the PIP control duct;

wherein the valve is configured to cycle between the first outlet port and the second outlet port thereby switching a flow of a gas from the inlet port to only the first outlet port and from the inlet port to only the second outlet port;

wherein a cycle corresponds to one breath; and wherein when the gas flows from the inlet port to the first outlet port of the valve, the gas flows through the PIP control duct, thereby controlling a PIP in the system so that a patient receives the PIP, and when the gas flows from the inlet port to the second outlet port of the valve, the gas flows through the PEEP control duct, thereby lowering pressure in the system to a PEEP so that the patient receives the PEEP.

9. The apparatus of claim 8, further comprising a container containing the body of fluid, and the PIP control duct and the PEEP control duct are immersed in the body of fluid in the container.

10. The apparatus of claim 8, further comprising at least two containers wherein a first container contains a first body of fluid and a second container contains a second body of fluid, and the PIP control duct is immersed in the first body of fluid in the first container and the PEEP control duct is immersed in the second body of fluid in the second container.

11. The apparatus of claim 10, wherein a size and a shape of the first container is similar to a size and a shape of the second container and location of a tip of the PIP control duct in the first container is similar to location of a tip of the PEEP control duct in the second container.

12. The apparatus of claim 8, wherein a controller is communicably connected to the valve to control a rate of cycling of the valve, thereby controlling a number of breaths per minute, and to control at least one of (a) an inspiratory time in seconds, (b) a ratio of the inspiratory time to an expiratory time, and (c) the inspiratory time as a percentage of a cycle time, thereby maintaining the ratio of the inspiratory time to the expiratory time as determined by a user.

13. The apparatus of claim 8, wherein the valve has a coefficient of flow Cv greater than about 1.5.

14. The apparatus of claim 8, wherein the valve is a solenoid valve and the fluid comprises water.

15. The apparatus of claim 8, wherein at least one angled section is connected to a tip of at least one of the PIP control duct and the PEEP control duct.

16. A method of assisting breathing of a subject using an apparatus of claim 12, the subject selected from a group consisting of an adult, a child, an infant human being and a mammal, comprising:

(i) connecting the subject to the apparatus of claim 12;
(ii) initiating a flow of a gas in the apparatus; and
(iii) monitoring a number of breaths per minute delivered to the subject.

17. The method of claim 16, further comprising connecting the subject to the apparatus using nasal prongs, a face mask or a nasal mask.

18. The method of claim 16, further comprising setting the flow of the gas at about 1 to 10 L/min for the infant human being.

19. The method of claim 16, further comprising setting the flow of the gas at about 1 to 30 L/min for the adult human being.

20. The method of claim 16, further comprising selecting an immersed length of a PIP control duct and an immersed length of a PEEP control duct based on the subject's unique breathing needs.

21. The method of claim 20, further comprising controlling at least one of (a) an inspiratory time in seconds, (b) a ratio of the inspiratory time to an expiratory time, and (c) the inspiratory time as a percentage of a cycle time, thereby maintaining the ratio of the inspiratory time to the expiratory time as determined by a user.

* * * * *